US006184012B1

(12) United States Patent
Neri et al.

(10) Patent No.: US 6,184,012 B1
(45) Date of Patent: Feb. 6, 2001

(54) ISOLATION OF ENZYMES

(75) Inventors: Dario Neri; Salvatore Demartis; Adrian Huber; Francesca Viti, all of Zurich (CH); Dan S Tawfik; Gregory Paul Winter, both of Cambridge (GB)

(73) Assignee: Medical Research Council, London (GB)

(*) Notice: Under 35 U.S.C. 154(b), the term of this patent shall be extended for 0 days.

(21) Appl. No.: 09/142,355

(22) PCT Filed: Apr. 25, 1997

(86) PCT No.: PCT/GB97/01153

§ 371 Date: Apr. 22, 1999

§ 102(e) Date: Apr. 22, 1999

(87) PCT Pub. No.: WO97/40141

PCT Pub. Date: Oct. 30, 1997

(30) Foreign Application Priority Data

Apr. 25, 1996 (GB) .................................................. 9608540

(51) Int. Cl.[7] ............................... C12N 9/90; C12N 9/00

(52) U.S. Cl. ............................................ 435/188; 435/183

(58) Field of Search ..................................... 435/183, 188

(56) References Cited

U.S. PATENT DOCUMENTS 5,807,718 * 9/1998 Joyce et al. ......................... 435/91.5
5,910,408 * 6/1999 Szostak et al. .......................... 435/6

FOREIGN PATENT DOCUMENTS 7-126297 5/1995 (JP) .
WO 95/12672 5/1995 (WO) .
WO 96/17086 6/1996 (WO) .
WO 96/40723 12/1996 (WO) .
WO 97/09446 3/1997 (WO) .

OTHER PUBLICATIONS

P. Soumillion et al., 1994, Selection of Beta–Lactamase on Filamentous Bacteriophage by Catalytic Activity, J. Mol. Biol., 237:415–422.

M. Illangasekare, et al., Feb. 1995, Aminoacyl–RNA Synthesis Catalyzed by an RNA, Science, 267:643–647.

J.R. Lorsch and J.W. Szostak, 1994, In Vitro Evolution of New Ribozymes with Polynucleotide Kinase Activity, Nature, 371:31–36.

D.S. Tawfik, et al, 1993, Catelisa: A Facile General Route to Catalytic Antibodies, Proceedings of the Nat'l. Acad. of Sci., 90:373–377.

McCafferty, et al., 1991, Phage–enzymes: Expression and Affinity Chromatography of Functional Alkaline Phosphatase on the Surface of Bacteriophage, Protein Engineering, 4:995–961.

Corey, et al., 1993, Trypsin Display on the Surface of Bacteriophage, Gene 128:129–134.

* cited by examiner

*Primary Examiner*—Jon P. Weber
(74) *Attorney, Agent, or Firm*—Darby & Darby

(57) ABSTRACT

The present invention relates to a method of isolating an enzyme having a desired chemical or biological activity, the method comprising linking the enzyme to a substrate for the enzyme, reacting the enzyme and substrate such that a product is produced which remains linked to the enzyme and isolating the enzyme by selectively isolating the product linked to the enzyme.

17 Claims, 6 Drawing Sheets

FIG. 2

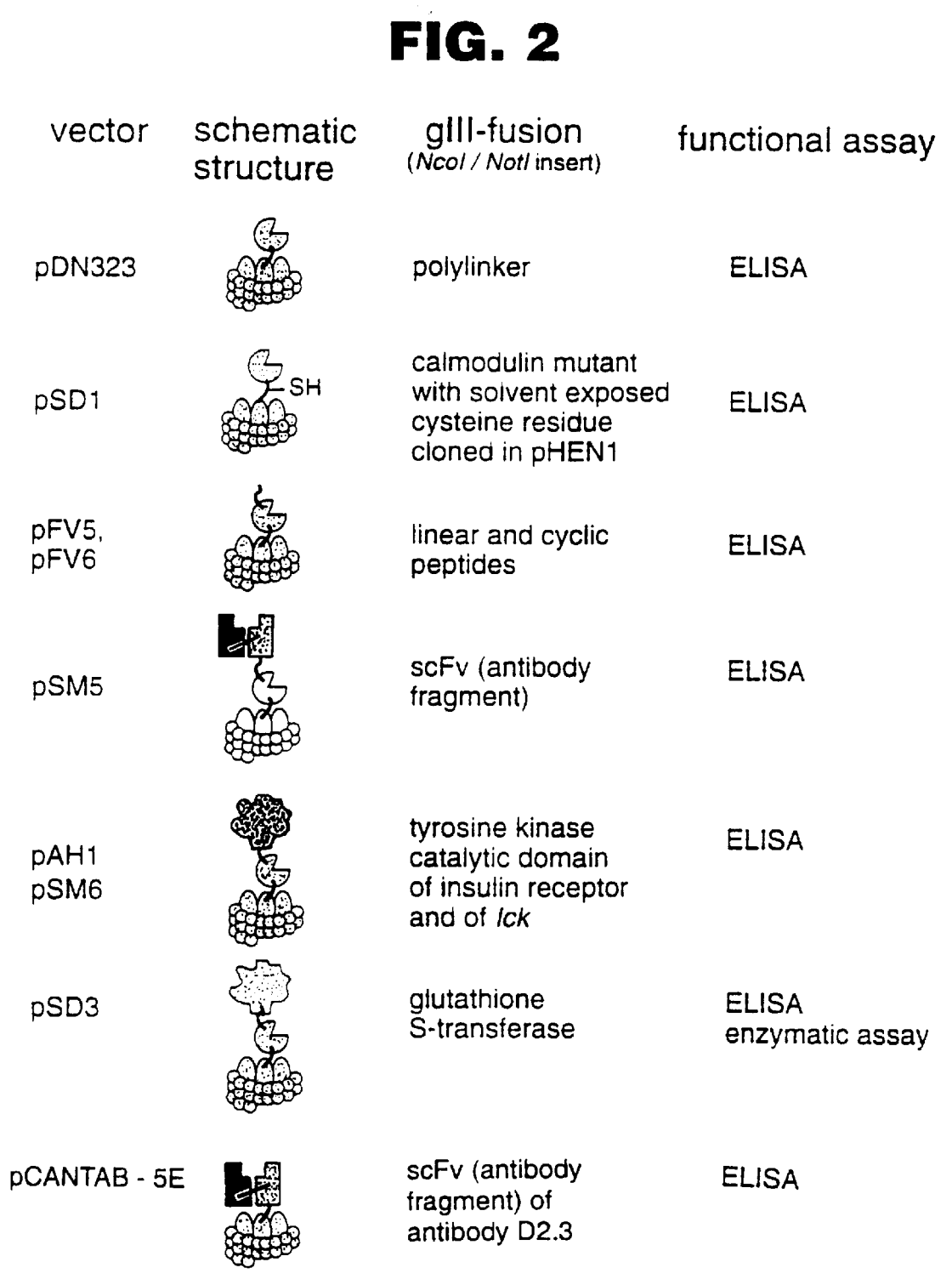

| vector | schematic structure | gIII-fusion (*NcoI / NotI* insert) | functional assay |
|---|---|---|---|
| pDN323 | | polylinker | ELISA |
| pSD1 | SH | calmodulin mutant with solvent exposed cysteine residue cloned in pHEN1 | ELISA |
| pFV5, pFV6 | | linear and cyclic peptides | ELISA |
| pSM5 | | scFv (antibody fragment) | ELISA |
| pAH1 pSM6 | | tyrosine kinase catalytic domain of insulin receptor and of *lck* | ELISA |
| pSD3 | | glutathione S-transferase | ELISA enzymatic assay |
| pCANTAB - 5E | | scFv (antibody fragment) of antibody D2.3 | ELISA |

SEQUENCE LISTING

```
<160> NUMBER OF SEQ ID NOS:  24

<210> SEQ ID NO 1
<211> LENGTH: 42
<212> TYPE: DNA
<213> ORGANISM: Artificial Sequence
<220> FEATURE:
<223> OTHER INFORMATION: Primer

<400> SEQUENCE: 1

agttccgcca tagcggccgc tgaccaactg acagaagagc ag                        42


<210> SEQ ID NO 2
<211> LENGTH: 39
<212> TYPE: DNA
<213> ORGANISM: Artificial Sequence
<220> FEATURE:
<223> OTHER INFORMATION: primer

<400> SEQUENCE: 2

ctttcaacag tctactttgc tgtcatcatt tgtacaaac                            39


<210> SEQ ID NO 3
<211> LENGTH: 41
<212> TYPE: DNA
<213> ORGANISM: Artificial Sequence
<220> FEATURE:
<223> OTHER INFORMATION: primer

<400> SEQUENCE: 3

caaatgatga cagcaaagta gactgttgaa agttgtttag c                         41


<210> SEQ ID NO 4
<211> LENGTH: 17
<212> TYPE: DNA
<213> ORGANISM: Artificial Sequence
<220> FEATURE:
<223> OTHER INFORMATION: primer

<400> SEQUENCE: 4
```

-continued gtaaaacgac ggccagt 17

<210> SEQ ID NO 5
<211> LENGTH: 48
<212> TYPE: DNA
<213> ORGANISM: Artificial Sequence
<220> FEATURE:
<223> OTHER INFORMATION: primer

<400> SEQUENCE: 5
agatcaattg ctctcgagac cacatgctgt catcatttgt acaaactc 48

<210> SEQ ID NO 6
<211> LENGTH: 17
<212> TYPE: DNA
<213> ORGANISM: Artificial Sequence
<220> FEATURE:
<223> OTHER INFORMATION: primer

<400> SEQUENCE: 6
caggaaacag ctatgac 17

<210> SEQ ID NO 7
<211> LENGTH: 65
<212> TYPE: DNA
<213> ORGANISM: Artificial Sequence
<220> FEATURE:
<223> OTHER INFORMATION: primer

<400> SEQUENCE: 7
gagtcattct gcggccgcct tgtcatcgtc gtccttgtag tcctgcagct gcacctgggc 60
catgg 65

<210> SEQ ID NO 8
<211> LENGTH: 65
<212> TYPE: DNA
<213> ORGANISM: Artificial Sequence
<220> FEATURE:
<223> OTHER INFORMATION: primer
<221> NAME/KEY: unsure
<222> LOCATION: n at 23...39
<223> OTHER INFORMATION: n is a or g or c or t/u, unknown or other
<221> NAME/KEY: unsure
<222> LOCATION: m at 22...37
<223> OTHER INFORMATION: m is a or c

<400> SEQUENCE: 8
gagtcattct gcggccgcac amnnmnnmnn mnnmnnmnna cactccagct gcacctgggc 60
catgg 65

<210> SEQ ID NO 9
<211> LENGTH: 53
<212> TYPE: DNA
<213> ORGANISM: Artificial Sequence
<220> FEATURE:
<223> OTHER INFORMATION: primer

<400> SEQUENCE: 9
atcgacccat ggcccaggtg tcctctctgt ttgtgccgga cgagtggcag gtg 53

<210> SEQ ID NO 10
<211> LENGTH: 43
<212> TYPE: DNA
<213> ORGANISM: Artificial Sequence
<220> FEATURE:
<223> OTHER INFORMATION: primer -continued

<400> SEQUENCE: 10
gagtcattct gcggccgcct cctcactctc gggagccttg ttc 43

<210> SEQ ID NO 11
<211> LENGTH: 42
<212> TYPE: DNA
<213> ORGANISM: Artificial Sequence
<220> FEATURE:
<223> OTHER INFORMATION: primer

<400> SEQUENCE: 11
atgcaatgat gcggccgcag gctgaggctg gtactggccc tc 42

<210> SEQ ID NO 12
<211> LENGTH: 45
<212> TYPE: DNA
<213> ORGANISM: Artificial Sequence
<220> FEATURE:
<223> OTHER INFORMATION: primer

<400> SEQUENCE: 12
tctatagcca tggcccaggt gcagaagccc cagaagccgt ggtgg 45

<210> SEQ ID NO 13
<211> LENGTH: 48
<212> TYPE: DNA
<213> ORGANISM: Artificial Sequence
<220> FEATURE:
<223> OTHER INFORMATION: primer

<400> SEQUENCE: 13
aatcgaccca tggcccaggt ccagatgtcc cctatactag gttattgg 48

<210> SEQ ID NO 14
<211> LENGTH: 41
<212> TYPE: DNA
<213> ORGANISM: Artificial Sequence
<220> FEATURE:
<223> OTHER INFORMATION: primer

<400> SEQUENCE: 14
gagtcattct gcggccgcgg atccacgcgg aaccagatcc g 41

<210> SEQ ID NO 15
<211> LENGTH: 23
<212> TYPE: PRT
<213> ORGANISM: Unknown
<220> FEATURE:
<223> OTHER INFORMATION: calmodulin binding peptide

<400> SEQUENCE: 15

Cys Ala Ala Ala Arg Trp Lys Lys Ala Phe Ile Ala Val Ser Ala Ala
1 5 10 15

Asn Arg Phe Lys Lys Ile Ser
20

<210> SEQ ID NO 16
<211> LENGTH: 23
<212> TYPE: PRT
<213> ORGANISM: Unknown
<220> FEATURE:
<223> OTHER INFORMATION: calmodulin binding peptide

<400> SEQUENCE: 16

-continued

```
Cys Ala Ala Ala Arg Ala Lys Lys Asn Phe Ile Ala Val Ser Ala Ala
 1               5                  10                  15

Asn Arg Phe Lys Lys Ile Ser
            20


<210> SEQ ID NO 17
<211> LENGTH: 29
<212> TYPE: PRT
<213> ORGANISM: Unknown
<220> FEATURE:
<223> OTHER INFORMATION: calmodulin binding ligand chimera

<400> SEQUENCE: 17

Glu Pro Gln Tyr Glu Glu Ile Gly Ala Ala Arg Trp Lys Lys Ala Phe
 1               5                  10                  15

Ile Ala Val Ser Ala Ala Asn Arg Phe Lys Lys Ile Ser
            20                  25


<210> SEQ ID NO 18
<211> LENGTH: 29
<212> TYPE: PRT
<213> ORGANISM: Unknown
<220> FEATURE:
<223> OTHER INFORMATION: calmodulin binding ligand chimera

<400> SEQUENCE: 18

Glu Pro Gln Phe Glu Glu Ile Gly Ala Ala Arg Trp Lys Lys Ala Phe
 1               5                  10                  15

Ile Ala Val Ser Ala Ala Asn Arg Phe Lys Lys Ile Ser
            20                  25


<210> SEQ ID NO 19
<211> LENGTH: 33
<212> TYPE: PRT
<213> ORGANISM: Unknown
<220> FEATURE:
<223> OTHER INFORMATION: calmodulin binding region and kinase substrate
                         sequence with a spacer

<400> SEQUENCE: 19

Thr Gly Asp Tyr Met Asn Met Ser Pro Val Gly Ala Ala Ala Arg Trp
 1               5                  10                  15

Lys Lys Ala Phe Ile Ala Val Ser Ala Ala Asn Arg Phe Lys Lys Ile
            20                  25                  30

Ser


<210> SEQ ID NO 20
<211> LENGTH: 25
<212> TYPE: PRT
<213> ORGANISM: Unknown
<220> FEATURE:
<223> OTHER INFORMATION: calmodulin binding peptide derivative

<400> SEQUENCE: 20

Cys Gly Gly Ala Ala Ala Arg Trp Lys Lys Ala Phe Ile Ala Val Ser
 1               5                  10                  15

Ala Ala Asn Arg Phe Lys Lys Ile Ser
            20                  25


<210> SEQ ID NO 21
<211> LENGTH: 17
<212> TYPE: DNA
<213> ORGANISM: Artificial Sequence
<220> FEATURE:
```

-continued

```
<223> OTHER INFORMATION: primer

<400> SEQUENCE: 21

gaattttctg tatgagg                                                17


<210> SEQ ID NO 22
<211> LENGTH: 50
<212> TYPE: DNA
<213> ORGANISM: Artificial Sequence
<220> FEATURE:
<223> OTHER INFORMATION: primer

<400> SEQUENCE: 22

caagacttct ggatacatct tctgcagcta ctggattcac tgggtaaaac            50


<210> SEQ ID NO 23
<211> LENGTH: 25
<212> TYPE: DNA
<213> ORGANISM: Artificial Sequence
<220> FEATURE:
<223> OTHER INFORMATION: primer

<400> SEQUENCE: 23

gcagaagatg tatccagaag tgttg                                       25


<210> SEQ ID NO 24
<211> LENGTH: 18
<212> TYPE: DNA
<213> ORGANISM: Artificial Sequence
<220> FEATURE:
<223> OTHER INFORMATION: primer

<400> SEQUENCE: 24

ttggagattt tcaacgtg                                               18
```

ISOLATION OF ENZYMES

FIELD OF THE INVENTION

The present invention relates to constructs and methods for the generation, detection, and isolation of enzymes possessing a desired chemical or biological activity. In particular it relates to a method for the generation, detection and isolation of enzymes or proteins with enzyme-like activity, with a novel substrate or reaction specificity or with improved activity. In addition, the invention permits the subsequent identification and isolation of the nucleic acid encoding the enzyme.

BACKGROUND OF THE INVENTION

A number of different approaches have hitherto been taken to generate novel polypeptides with new, modified, or improved biological activity. For example, the alteration of individual residues at the active site of enzymes of known crystallographic structure (Winter et al., 1982; Wilkinson et al., 1984), immunization with transition state analogues (Tramontano et al., 1986) the screening of mutant microorganisms harbouring new properties (Cunningham and Wells, 1987), the alteration of specific residues within a signal peptide window and the generation of novel antibodies by phage display (Marks et al., 1994) have all led to the generation of polypeptides with tailored functions.

Antibody fragments have been expressed bacterially and in bacteriophage (phage) display repertoires by fusion to phage coat proteins, in particular the minor coat protein cpIII. Subsequent selection of phage with antigen has allowed the isolation of high affinity antibodies from large libraries without immunisation.

The endogenous genetic machinery of phage, and the ability to generate a large population of individually unique phage clones means that a huge ($>10^8$) variety of different recombinant polypeptides can be produced. A large number of variants of a certain polypeptide chain are cloned into the genome of filamentous phage or constructed as phagemids and expressed as a fusion protein with the phage coat protein. This library is then selected by panning to the ligand of interest; after extensive washings and elution, those phages expressing a binding variant are rescued by infection of bacteria. Multiple rounds of selection allow the isolation of very rare phage ($<1/10^7$).

Phage display has also been used as a tool to investigate the relative efficacy of signal peptides, to evaluate the individual contribution of each residue of an epitope, and to refine the properties of such biological molecules. For example, phage display has been used to isolate zinc finger domains with altered DNA-binding specificity, improved hormones and novel inhibitors.

The generation of novel enzymes, or enzymes with improved function has proven more difficult. The main obstacles in this case are associated with methods of selection. In nature, new enzymes arise through random mutation and Darwinian selection. Initial attempts to mimic this process used mutant microorganisms, selecting for increased enzyme activity by growth advantage (Cunningham and Wells, 1987). More recently, both alkaline phosphatase and trypsin have been displayed on the surface of phage, and have been shown to retain their catalytic activity (McCaf ferty et al., 1991, Corey et al., 1993). Such phages have been enriched by binding to suicide inhibitors that bind irreversibly to the protein. Soumillion et al., 1994 describe incubation of phage displaying a β-lactamase with a β-lactamase suicide inhibitor connected by a spacer to a biotin moiety. Active phages were selected by binding and elution from streptavidin-coated beads. Such a procedure suffers from the drawback that a suicide inhibitor or a transition state analogue must be available for the reaction of interest. This is not generally the case. Moreover, indirect selections result in low rate accelerations. A direct selection for the desired catalytic activity would yield better results.

SUMMARY OF THE INVENTION

According to the present invention, there is provided a method of isolating an enzyme having a desired chemical or biological activity the method comprising:

a) linking the enzyme to a substrate for the enzyme;

b) reacting the enzyme with the substrate such that a product is produced which remains linked to the enzyme; and c) isolating the active enzyme by selectively isolating the product linked to the enzyme.

The invention also provides a method of isolating DNA encoding an enzyme comprising a) linking the enzyme to a substrate for the enzyme; b) reacting the enzyme and substrate such that a product is produced which remains linked to the enzyme; and c) isolating the enzyme by selectively isolating the product linked to the enzyme; wherein the enzyme is further linked to DNA encoding the enzyme.

According to a further aspect of the present invention there is also provided a composition comprising an enzyme linked to a substrate for the enzyme or linked to a product of the reaction between the enzyme and the substrate.

BRIEF DESCRIPTION OF THE DRAWINGS

FIG. 2 lists the names of the constructed phagemids, along with schematic structures depicting the proteins that each phagemid encodes.

Squares: CAAARWKKAFIAVSAANRFKKIS (SEQ ID NO:15);

Circles: CAAARAKKNFIAVSAANRFKKIS (SEQ ID NO:16).

Figure 6:
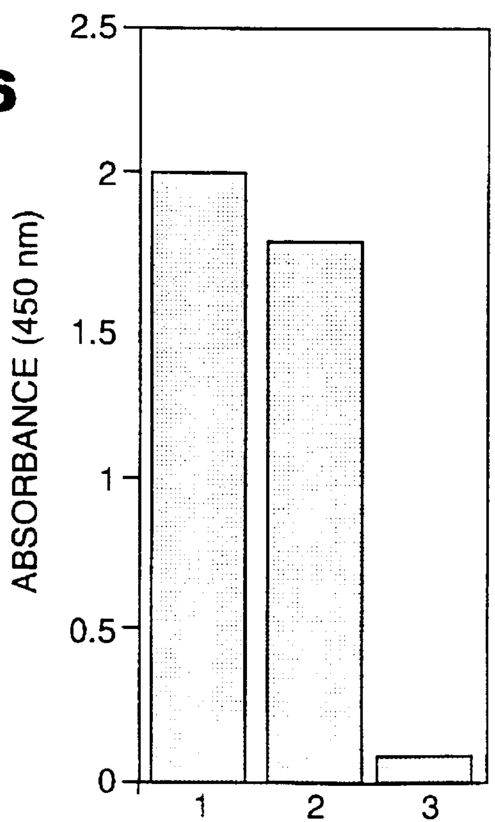

FIG. 6 shows the results of an ELISA assay illustrating the stability of calmodulin-tagged phage DN323/biotin-CAAARWKKAFIAVSAANRFKKIS (SEQ ID NO: 15) complex upon PEG precipitation as detected by ELISA. (1) Before PEG precipitation. (2) After PEG precipitation. (3) 2% milk in TBSC instead of phage.

Figure 7:
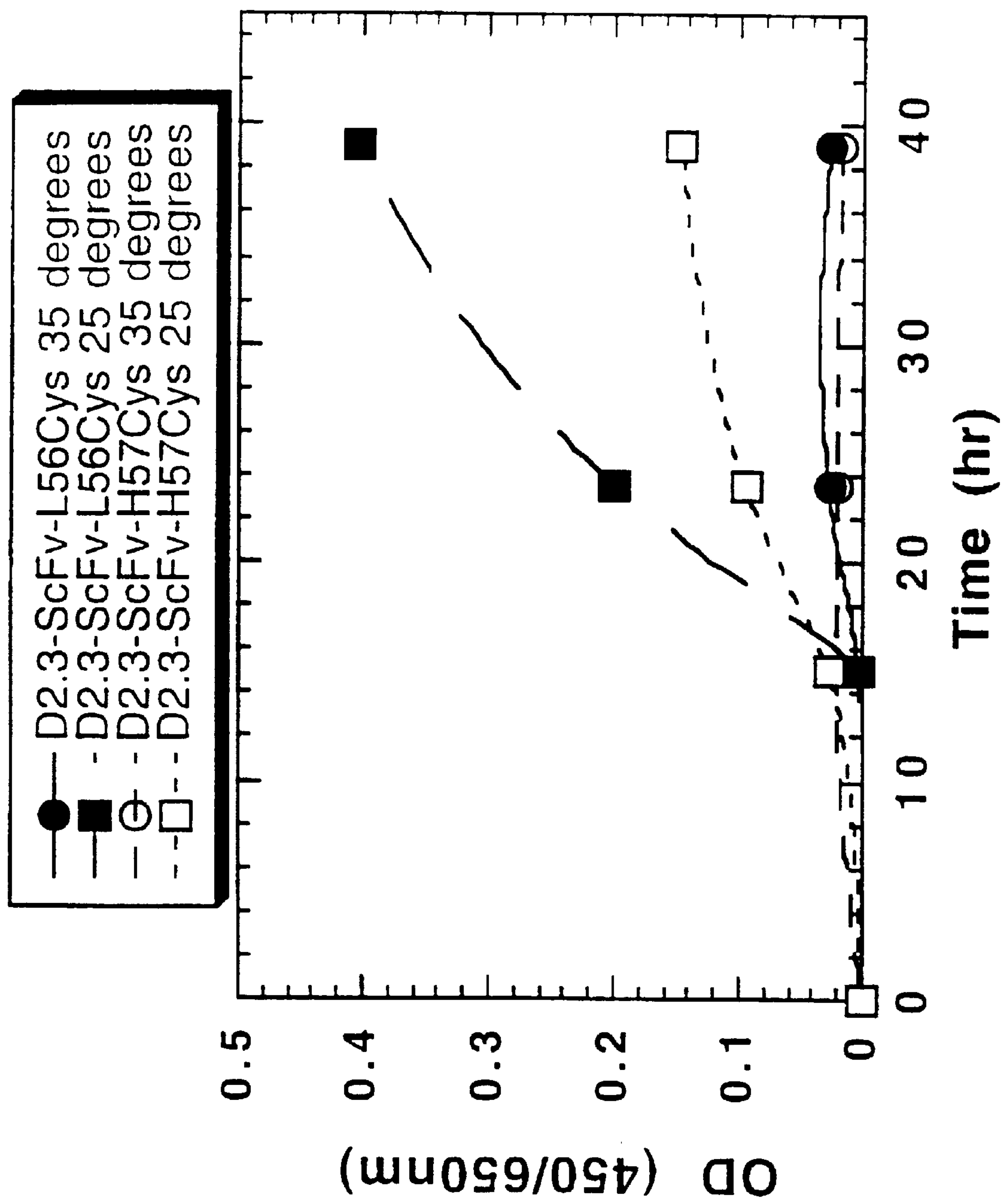

FIG. 7 shows the growth of bacteria at various temperatures.

Figure 8:
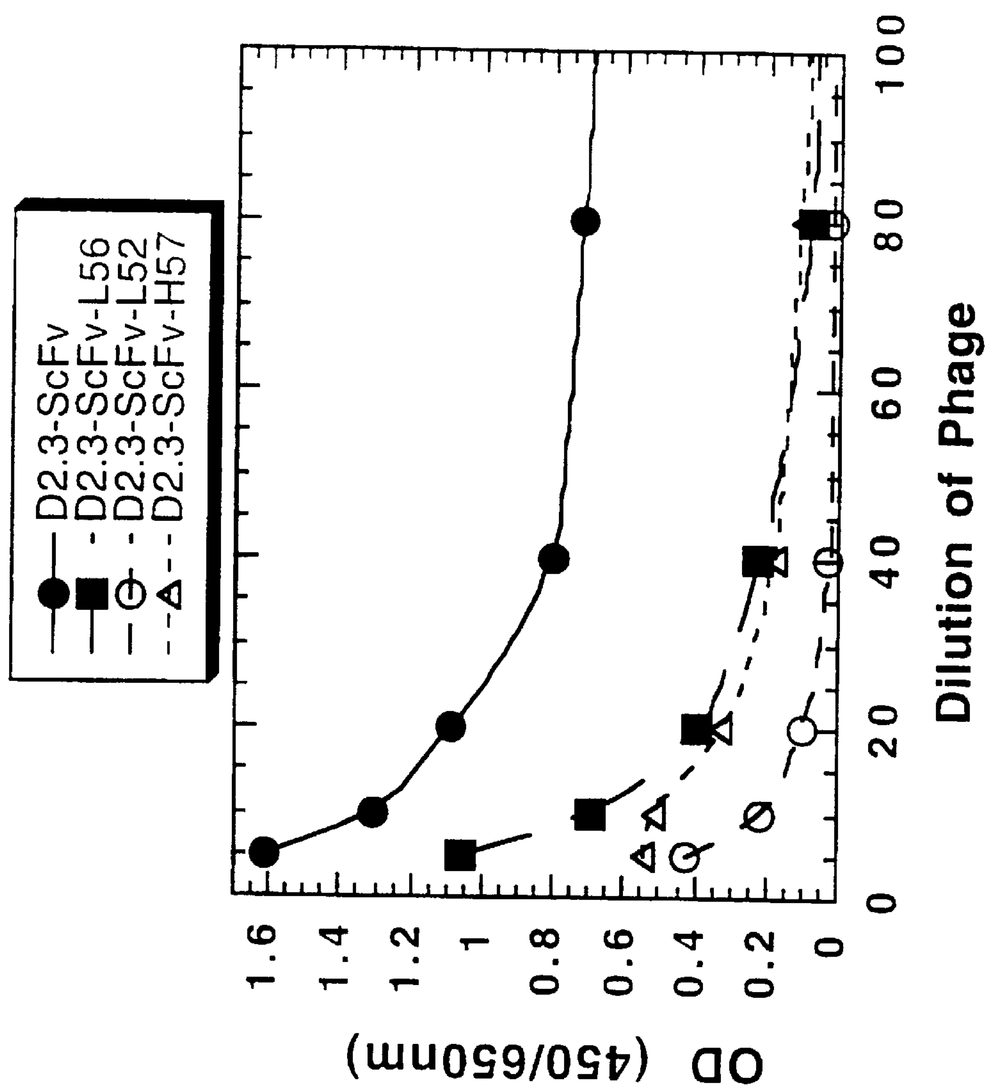

FIG. 8 shows the results of the phage ELISA.

The term "enzyme" as used herein refers to any molecule capable of accelerating the rate of conversion of a substrate to a product, such that the product of the reaction is distinguishable from the substrate. Preferably, the enzyme comprises a polypeptide.

The conversion of the substrate to the product may comprise a physical or chemical change. For example, the conversion may comprise the modification, addition or removal of one or more chemical groups. Modification of the substrate includes any disproportion, rearrangement or isomerization that lends different properties to the product compared to those of the substrate. The modification of substrate may also be through a conformational change. For example, contact of an enzyme with a substrate such as a protein may result in the induction of a temporary or permanent conformational change in that substrate. Such a change may allow the isolation of product from the substrate within the lifetime of the conformationally-altered state.

In an alternative embodiment, the substrate may comprise a polypeptide linked to the enzyme via a peptide bond in a fusion protein. Knowledge of the position of the active site in the tertiary structure of the enzyme may allow the introduction of DNA encoding a peptide substrate into the gene sequence of the enzyme. Most commonly this will be introduced at the carboxy or amino terminus end of the enzyme, but can also be included as a "window" loop. When the substrate is converted intramolecularly to product, this remains bound to the enzyme and allows isolation of the enzyme.

In the present invention the substrate is physically or chemically linked to the enzyme such that upon reaction of the enzyme with the substrate, the substrate, and subsequently the product remains physically or chemically linked to the enzyme. By maintaining a link between the enzyme and the product, the product provides a "handle" by which active enzyme may be isolated from the reaction mixture. The present invention permits, for example, separation of active enzyme from enzyme libraries. Further rounds of selection may be used to select for enzymes with improved or modified activity.

The substrate may be linked to the enzyme by any suitable means which permits reaction of the enzyme with the substrate. Preferably, the enzyme and substrate are linked by a flexible linker which permits association of the substrate with the active site of the enzyme, reaction of the enzyme with the substrate to produce the product and subsequent dissociation of the product from the active site of the enzyme. Preferably, the substrate/product is linked to the enzyme at a site outside, but in the vicinity of the active site of the enzyme in a manner that interferes minimally with the chemical or biological activity of the enzyme.

By "active" site of the enzyme is meant the region in the tertiary structure of the protein at which conversion of substrate to product takes place.

The linker may comprise a covalent linker such as a hydrocarbon chain, an aliphatic, heteroaliphatic, aromatic or heteroaromatic chain, a polymeric chain or a polypeptide or nucleic acid chain.

The linker between the enzyme and the substrate/product may be entirely covalent. The advantage of using such a covalent linker is that a strong link is maintained between product and enzyme. This aspect of the invention is therefore particularly useful for the isolation of enzymes which have a very slow reaction time.

The linker may be linked to the enzyme and substrate via any suitable functional groups present in the linker, enzyme and substrate. For example, where the enzyme is a protein the linker may be linked to the enzyme via a peptide linkage or via functional groups, such as thiol, hydroxy, amino and aromatic group, present in the side chains of the amino acids of the protein.

The cysteine residue possesses a thiol group and is thus particularly suitable for use according to this aspect of the invention. A variety of reagents that react selectively with the thiol group of a cysteine are available (Hermanson, G. T., 1996). Moreover, the coat proteins of filamentous phages do not generally have many free thiols exposed on their surfaces. Similarly, reduced and exposed thiol groups (i.e., not in the form of disulphide bridges) are very uncommon in antibodies. Hence, introducing a mutation to cysteine in the vicinity of the antibody active site can allow the specific covalent linkage of a ligand that carries an appropriate thiol reactive group with little or no non-specific linking to other residues of the antibody or the phage particle.

The linker or part thereof may be produced as a fusion protein with the enzyme. Methods of construction of such fusion proteins by recombinant DNA technology are well known to those of skill in the art as illustrated, for example, in Sambrook et al. (1989).

According to a preferred embodiment of the invention, the linker comprises a binding pair. As used herein, the term binding pair refers to any pair of molecules capable of releasably binding to one another. Incorporation of a binding pair as part of the linker between the enzyme and substrate/product or as the linker itself is advantageous in that it permits easy linkage of the substrate or a modified substrate to the enzyme. It also permits easy release of the enzyme from the product after purification. Preferably, association and dissociation of the binding pair takes place under defined conditions such as temperature, concentration, solvent, ion concentration, such that linking and cleavage of the enzyme and substrate/product may be controlled by modification of the conditions.

Preferably, the enzyme and all or part of the linker comprise a fusion protein. Most preferably, the fusion protein comprises a fusion of the enzyme and calmodulin. By joining the substrate for the enzyme to a ligand for calmodulin, the substrate may be linked to the enzyme by means of the calmodulin-ligand binding pair interaction. It will be appreciated that each member of any binding pair, such as the calmodulin-ligand binding pair, may be used interchangeably with its counterpart. Thus, the enzyme may be linked to calmodulin and the substrate linked to a calmodulin ligand or vice versa.

A particular feature of the present invention is that it permits selection and isolation of an enzyme on the basis of its phenotype (ie enzymatic activity) while coupled to its corresponding genotype (e.g. DNA encoding the enzyme).

Thus, according to a further aspect of the present invention, there is provided a method of isolating DNA encoding an enzyme comprising linking the enzyme to a substrate for the enzyme; reacting the enzyme with the substrate such that a product is produced which remains linked to the enzyme; and isolating the enzyme by selectively isolating the product linked to the enzyme; wherein the enzyme is further linked to DNA encoding the enzyme.

The enzyme may be displayed on the surface of a support containing a DNA sequence encoding the enzyme. The support may comprise any suitable cell, phage or particle capable of containing a DNA sequence encoding the enzyme, expressing the DNA encoding the enzyme and displaying the enzyme on its surface. Suitable host cells include eukaryotic or prokaryotic cells such as bacterial, mammalian, yeast and baculoviral systems. Suitable bacterial cells include *E. coli* and many others. Suitable mammalian cell lines available for expression of a heterologous fusion peptide include HeLa cells, Chinese hamster ovary cells, COS cells and many others. The choice of cell line will be dependent on the particular characteristics of the expressed protein, and the levels of expression required. Suitable particles include viral and retroviral systems, such as baculovirus, and phage particles.

Preferably, the support comprises a filamentous bacteriophage. Filamentous bacteriophage may be used to display the enzyme by fusion of the enzyme to a coat protein such as the minor g3p (Smith, 1985; Bass et al., 1990; McCafferty et al., 1990) minor g6p (Jespers et al., 1995) or major (g8p) (Kang et al., 1991) coat proteins.

The gene encoding the displayed enzyme can be isolated by selecting for the enzyme product which is linked to the enzyme which in turn is linked to the phage particle which comprises the gene. The gene may be amplified by growth of the phage.

The isolation of active enzyme may be performed by any method that allows separation of the enzyme product from unchanged enzyme substrate. The method may comprise chemical or physical separation techniques.

The physical properties (such as solubility) of the substrate and product may be sufficiently different that direct physical separation of the enzyme-product conjugate from the enzyme-substrate conjugate is possible. The difference in the physical properties may be enhanced by selective chemical modification or derivatisation of the enzyme-product conjugate or enzyme-substrate-conjugate (Illangasekare et al., 1995). Alternatively, separation may be accomplished by selective chemical reaction of the enzyme-product conjugate or enzyme-substrate conjugate with a reactive chemical moiety bound to a solid matrix (Lonsch & Szostak, 1992).

A site for cleavage, for example by a specific protease, may be incorporated in the linker. Suitable proteases include Factor Xa (EP 0 161 937) and enterokinase (EP 0 035 384). This provides a means for the release of the enzyme from the product following purification.

Where the enzyme-product conjugate and enzyme-substrate conjugates are linked to cells or particles such as phage particles, they may be physically separated for example by the techniques of antibody panning, rosetting, agglutination, precipitation or by fluorescence activated cell sorting (FACS).

Preferably, enzyme-product conjugate and enzyme-substrate conjugate may be separated by biopanning on immunotubes coated with a suitable affinity reagent, or by affinity chromatography using a solid matrix to which is bound an affinity reagent, such as an antibody, capable of selectively binding the enzyme-product conjugate or the substrate-enzyme conjugate (Tawfik et al., 1993; Tawfik et al., 1997). The affinity matrix may comprise any suitable solid support such as a resin, beads or any other conventional matrix. The affinity matrix may selectively bind the substrate-enzyme conjugate such that the product-enzyme conjugate remains in the elute. Preferably however, the affinity reagent selectively binds the product-enzyme conjugate such that the substrate-enzyme conjugate is completely removed by washing. The product-enzyme conjugate may be recovered from the affinity matrix by use of appropriate desorption conditions such as low pH, raised salt concentration or competitive binding.

Where the enzyme is linked to the product via a binding pair, the enzyme may be released from the affinity matrix under conditions which cause dissociation of the binding pair.

The binding affinity of the two members of the binding pair should be strong enough to survive the enzymatic conversion of the substrate to the product and the purification strategy employed for the isolation of product. The binding affinity of the two members of the binding pair may be defined in terms of the dissociation constant ($K_d$) for the interaction wherein:

$$K_d = k_{off}/k_{on}$$

where $k_{on}$ is the kinetic association constant of the reaction and $k_{off}$ is the kinetic dissociation constant of the reaction Preferably, the binding pair employed in the present invention has a dissociation constant ($K_d$) of 10 nM or less, more preferably 1 nM or less, measured at a pH of between 6 and 9 at 20° C.

Alternatively, the kinetic stability of the association of the binding pair may be measured. This may be defined in terms of the half-life $t_{1/2}$ of the complex in conditions of irreversible dissociation wherein:

$$t_{1/2} = 1/k_{off}$$

The half-life of this interaction should be of sufficient length to allow for the conversion of substrate to product, and purification of product. Preferably, the half-life of the interaction is at least 15 minutes, preferably at least one hour.

Examples of binding pairs that may be used in the present invention include an antigen and an antibody or fragment thereof capable of binding the antigen, the biotin-streptavidin binding pair, a protein and an inhibitor capable of binding the protein such as an RNase and an RNase inhibitor (eg RNasin or barstar) and a calcium-dependent binding polypeptide and ligand thereof.

Preferably, the binding pair comprises a calcium-dependent binding protein and ligand thereof, wherein the binding of the protein and ligand is dependent upon the concentration of calcium ions. By this is meant that the dissociation constant for the ligand is reduced in the presence of calcium ions, that is, binding is much stronger in the presence of calcium ions. For the applications described herein it is preferred that this reduction is at least ten-fold where the binding protein has one tenth of its calcium binding sites occupied. Preferably, the dissociation constant is greater than 10 nM in the absence of calcium ions and 10 nM or less in the presence of calcium ions, preferably 1 nM or less, at a pH of between 6 and 9 at 20° C. The mutual affinity of the binding pair may be modulated by the addition of calcium chelators such as EGTA, or EDTA. For some calcium dependent binding proteins, other analogous ions may replace calcium, for example strontium.

The calcium-dependent binding protein of choice is calmodulin, a small protein of 148 residues. Calmodulin is very resistant to denaturation and contains no disulphide bridges within the protein sequence, meaning that it can be expressed in bacteria and phage. Several proteins, peptides and organic compounds bind to calmodulin with high affinity (nM or sub nM). These ligands include calmidazolium, melittin, NO-30, AC-28, melatonin, (skeletal) myosin light chain kinase, and mastaporan. The latter two and their derivatives are the preferred ligands in this application, since they both show high affinity for calmodulin, and the interaction has a long half-life. In addition, derivatives of these peptides in which substitutions replace wild type residues have been recently discovered (Montigiani et al., 1996; T örok and Trentham, 1994; O'Neal and DeGrado, 1989). Due to their helix-forming properties, such peptides bind to calmodulin with even greater affinity than do the wild type substrates, and thus are preferred candidates for use in this application (see Neri et al. (1996) J. Mol. Biol. in press and copending International Patent Application "Calcium dependent binding ligands" in the name of the Medical Research Coucil filed on the Apr. 25, 1997, the disclosures of which are incorporated herein by reference)

Other calcium-dependent binding proteins include troponin C, calcineurin, parvalbumin and oncomodulin. In addition, fragments, and derivatives of calcium dependent binding proteins that retain binding activity may be used. The term "derivative" includes variants containing amino acid deletions, substitutions, or insertions.

Preferably, the enzyme-linker conjugate is produced by expression from gene fusions. Nucleic acid encoding such molecules is provided by the present invention. Suitable vectors for the expression of such molecules can be chosen or constructed, containing suitable promoter sequences, enhancer sequences, ribosome binding sites, expression signals, polyadenylation signals, termination sequences, signal sequences, and appropriate marker genes. Host cells may then be grown in culture in vitro to cause or allow production of the fusion molecules.

The enzyme-calmodulin fusion protein of the present invention is linked to its encoding nucleic acid via a support. A support may be any species that allows the linkage of the enzyme to the nucleic acid that encodes it. This allows the simultaneous isolation of the encoding gene when the product of successful catalysis is identified, bound to the active enzyme.

Preferably, enzyme is displayed on the surface of phage. Phage is the preferred host for a number of reasons. First, as discussed above, large expression libraries may be generated by packaging of DNA into phage particles. Gene libraries encoding up to $10^9$ unique protein species may be produced, from any organism, tissue, cell type, or developmental stage. Second, fusion to a coat protein allows display of the enzyme to the surrounding medium. Thus, the active site is readily displayed to the substrate-ligand complex. Third, phage can be easily analyzed and clonally selected through infection and plaque assays. Also, once purified, a clonal phage population can be amplified to produce a high titre of infective units. The high infectivity that phage display towards bacteria allows the preparation of large amounts of phage-encoded protein within a specific bacterial strain.

The enzyme is displayed on the surface of phage by fusion to a phage coat protein. A preferred coat protein is the tail protein, pIII (Smith, 1985; Bass et al., 1990, McCafferty et al., 1990). Other fusion partners can be pVIII (Kang et al., 1991), or pVI (Jespers et al., 1995). The enzyme-calmodulin-pIII protein is produced by genetic fusion to the 3' end of the phage coat protein gene. A substrate-enzyme conjugate may be formed by binding the calmodulin-enzyme fusion to a ligand-substrate fusion via the calmodulin-ligand binding pair interaction.

The isolation of active enzyme may be performed by any method that allows the "capture" of product. In the preferred embodiment of the invention, affinity separation techniques are employed to enrich for members of the phage library that bind a target immobilized on a solid matrix. This target specifically binds the product of the catalysed reaction. Thus, inactive phage are washed from the support. Subsequent elution of active phage allows the clonal isolation and amplification of individual phage through infection of bacteria. Multiple rounds of selection make this approach extremely efficient.

The method of generation of the protein expression library may be through the use of vectors encoding nucleic acid species from cDNA libraries. Alternatively, one individual gene encoding one protein may be expressed in the phage population and exposed to mutagenesis using a repair-deficient strain of *E. coli* . This results in the production of a phage library displaying protein species mutated throughout the length of the sequence. Most of these will be inactive, or will be less catalytically efficient than the wild type protein. However, in a large library, some species may be produced that exhibit improved properties. These may be isolated by modification of the reaction conditions to favour the isolation of species with improved characteristics.

As referred to above, phage expressing active protein are isolated by binding to a target that itself binds the product of the reaction. The experimental parameters may be modified to allow the isolation of the most highly active phage enzyme. For enzymatic reactions this may be through modulation of parameters such as temperature, time of reaction, pressure, by using various concentrations of competitors or inhibitors, or by varying the length of the linker between enzyme and substrate. In this way only the most active phage convert substrate to product under the conditions used, and only these phage are isolated.

Fusion of recombinant enzyme with pVIII (of which there are ~2800 copies per cell) allows multivalent display of a protein derived from one nucleic acid species. Thus, product will be detected by the target reagent in conditions of higher stringency. In this way phage expressing recombinant protein species with lower activities may be isolated.

Various aspects and embodiments of the present invention are illustrated in the following examples with reference to the figures. Further aspects and embodiments of the present invention will be apparent to those skilled in the art.

All documents mentioned in the text are incorporated by reference.

EXAMPLES

Example 1

Construction of Recombinant Calmodulin Fusion Proteins

Initially, test experiments were run to check whether a calmodulin tag of pDN323 was compatible with protein display on filamentous phage. Linear and cyclic peptides, an antibody fragment and three enzymes were cloned into the phagemid pDN323. The structure of this phagemid is summarised in FIG. 1; it contains a calmodulin-pIII gene fusion and was constructed as follows.

The calmodulin gene and gene III of filamentous phage were PCR amplified using oligonucleotide pairs cambano/camg3 for and camg3back/LMB2, respectively (cambano: 5' AGT TCC GCC ATA GCG GCC GCT GAC CAA CTG ACA GAA GAG CAG 3' SEQ ID No. 1; camg3 for: 5' CTT TCA ACA GTC TAC TTT GCT GTC ATC ATT TGT ACA AAC 3' (SEQ ID NO: 2 ); camg3back: 5' CAA ATG ATG ACA GCA AAG TAG ACT GTT GAA AGT TGT TTA GC 3' (SEQ ID NO: 3); LMB2: 5' GTA AAA CGA CGG CCA GT 3'(SEQ ID NO: 4)); (94° C.{1'}–55° C.(1')–72° C. {2'}, 25 cycles). The resulting products were gel-purified, then assembled by PCR using oligonucleotides cambano and LMB2 (94° C. {1')–55° C. {1'}–72° C. {2'}, 25 cycles). The PCR assembly band of the expected size was purified using the Spin-bind kit (FMC, Rockland, Me.), then digested with Not1/EcoR1 and subcloned in Not1/EcoR1 digested pUC119SNpolymyc (Figini et al., 1994), to produce phagemid pDN323.

ScFv(MFE-23) (Chester et al., 1994) and scFv(D1.3) (McCafferty et al., 1990) were subcloned in the Sfi1/Not1 sites of pDN323, yielding phagemids pDN327 and pSM5, respectively.

pSD1 was obtained by PCR amplification of the calmodulin gene with oligos CAMBANCO and CAMCFOXHO (5'- AGA TCA ATT GCT CTC GAG ACC ACA TGC TGT CAT CAT TTG TAC AAA CTC -3' (SEQ ID NO: 5)), which append a cysteine containing tag at the C-terminus of calmodulin. The resulting fragment was then subcloned in the NcoI/XhoI sites of pHEN1.

pFV5, which allows the display of the FLAG linear peptide (Hopp et al., 1988) on calmodulin-tagged phage, was obtained by PCR amplification using primers LMB3 (5'- CAG GAA ACA GCT ATG AC -3' (SEQ ID NO: 6)) and FLAGNOT (5'- GAG TCA TTC TGC GGC CGC CTT GTC ATC GTC GTC CTT GTA GTC CTG CAG CTG CAC CTG GGC CAT GG -3' (SEQ ID NO: 7)) and pHEN1 as template. The resulting product was subcloned into the HindIII/NotI sites of pDN323.

pFV6 was obtained by PCR amplification using primers LMB3 and FVCX6CNOT (5'- GAG TCA TTC TGC GGC CGC ACA MNN MNN MNN MNN MNN MNN ACA CTG CAG CTG CAC CTG GGC CAT GG -3' (SEQ ID NO: 8)). The resulting product was subcloned into the HindIII/NotI sites of pDN323. This resulted in a plasmid library expressing a variety of cyclic peptides displayed on calmodulin-tagged phage.

pAH1: the catalytic domain of the insulin receptor tyrosine kinase domain (Hubbard et al., 1994) was PCR amplified with oligos IRKBANCO (5'- ATC GAC CCA TGG CCC AGG TGT CCT CTG TGT TTG TGC CGG ACG AGT GGG AGG TG -3' (SEQ ID NO: 9)) and IRKFONOT (5'- GAG TCA TTC TGC GGC CGC CTC CTC ACT CTC GGG AGC CTT GTT C -3' (SEQ ID NO: 10)), then subcloned into the the NcoI/NotI sites of pDN323. The same insert, subcloned into the NcoI/NotI sites of pCANTAB6 (Vaughan et al., 1996), yielded vector pAH2.

pSM6: the catalytic domain of the 1 ck tyrosine kinase domain was PCR amplified with oligos LCKFONOT (5'- ATG CAA TGA TGC GGC CGC AGG CTG AGG CTG GTA CTG GCC CTC -3' (SEQ ID NO: 11)) and LCKBANCO (5'- TCT ATA GCC ATG GCC CAG GTG CAG AAG CCC CAG AAG CCG TGG TGG -3' (SEQ ID NO: 12)), then subcloned into the NcoI/NotI sites of pDN323.

pSD3: the glutathione S-transferase gene from S. japonica was PCR amplified from vector pGEX-4T (Pharmacia Biotech, Piscataway, N.J., U.S.A.) with oligos GSTBANCO (5'- AAT CGA CCC ATG GCC CAG GTC CAG ATG TCC CCT ATA CTA GGT TAT TGG -3' (SEQ ID NO: 13)) and GSTFONOT1 (5'- GAG TCA TTC TGC GGC CGC GGA TCC ACG CGG AAC CAG ATC CG -3' (SEQ ID NO: 14)), then subcloned into the NcoI/NotI sites of pDN323. The same insert, subcloned into the NcoI/NotI sites of pCANTAB6 (Vaughan et al., 1996), yielded vector pFV7.

pCANTAB-5E (Se-Ho Kim, Ph.D thesis, Weizmann Institute of Science, 1997) was a gift from Prof. Zelig Eshhar and Mr. Se-Ho Kim from the Weizmann Institute of Science, Rehovot, Israel. This plasmid contains DNA encoding the ScFv portion of antibody D2.3. This antibody was elicited by immunisation with a p-nitrobenzyl phosphonate tranition state analogue (NBP), cloned as part of the pIII filamentous phage coat protein gene.

FIG. 2 lists the names of the constructed phagemids, long with schematic structures depicting the proteins that each phagemid encodes.

Example 2

Calmodulin fusion proteins can successfully be displayed on phage and the resulting particles are infectious.

From the vectors described in Example 1, the corresponding phage particles were produced using standard procedures (Nissim et al., 1994). In all cases tested, high phage titres were obtained (>$10^{10}$ transforming units/ml, as measured in terms of colony forming units by infection of exponential TG1 bacteria) indicating that the calmodulin tag had no deleterious effect on phage production.

Example 3

Functional Activity of the Proteins Displayed on Phage.

Figure 1:
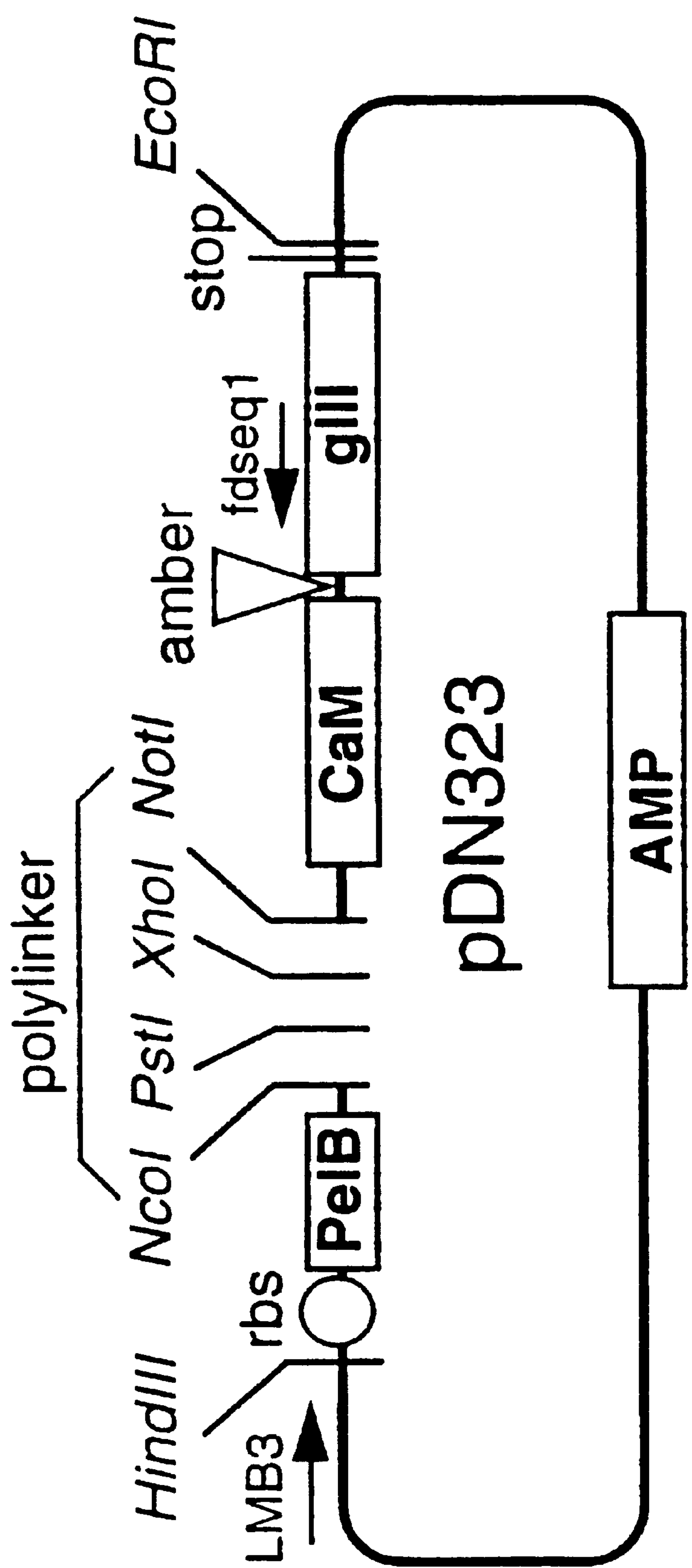
FIG. 1 shows a schematic diagram of phagemid pDN323.

The phage preparations of FIG. 1 were tested for the functional activity of both calmodulin and the proteins displayed on phage, using enzyme-linked immunosorbent assays (ELISA).

Phage ELISA assays were performed essentially as described (Nissim et al., 1994), but using a commercially available horseradish peroxidase-labeled anti-M13 antibody (Cat. Nr. 27-9411-01; Pharmacia Biotech, Piscataway, N.J., U.S.A.) as detecting reagent. Calmodulin binding activity was assayed using streptavidin-coated plates (Cat. No. 1645 492; Boehringer Mannheim, Germany), which had been incubated for 10 min. at room temperature (r.t.) with 100 $\mu$l of a $10^{-7}$M solution of biotin-labeled CAAARWKKAFIAVSAANRFKKIS (SEQ ID NO: 15) peptide (Montigiani et al., 1996) in phosphate buffered saline (50 mM phosphate, pH 7.2, 100 mM NaCl; PBS). The plates were then washed three times with PBS, blocked for 20 minutes with 2% skimmed milk in PBS (2% MPBS), then washed three times with PBS and used for ELISA. Binding assays in the presence of $Ca^{2+}$ were performed by adding to each well 30 $\mu$l 10% skimmed milk in TBSC (50 mM Tris-HCl, pH 7.4, 100 mM NaCl, 1 mM $CaCl_2$)+80 $\mu$l phage in TBSC ($10^{12}$ transforming units/ml). After 30 minutes incubation at r.t., plates were washed 5 times with TBSC+0.1% Tween-20, and 5 times with TBSC. To each well, horseradish peroxidase-labeled anti-M13 antibody (diluted 1:2000 in 2% milk dissolved in TBSC) was then added. After 20 minutes incubation, the plates were washed 5 times with TBSC+0.1% Tween-20, and 5 times with TBSC. Then, plate-bound peroxidase was detected with the ready-to-use BM-Blue soluble substrate (Cat. No. 1484281; Boehringer Mannheim, Germany). Binding in the absence of $Ca^{2+}$ was tested in a similar fashion, but replacing TBSC with TBSE (50 mM Tris-HCl, pH 7.4, 100 mM NaCl, 20 mM EDTA) in all the steps.

For the other ELISA assays, antigens were coated on microtitre plates (Cat. No. Falcon 3912, Becton Dickinson Labware, Oxnard, Calif., U.S.A.) overnight at r.t. as follows: anti-FLAG M2 antibody (Kodak), 5 $\mu$g/ml; hen egg lysozyme (Sigma, St. Louis, Mo., U.S.A.), 3mg/ml; anti-GST monoclonal antibody GST-2 ascites (Cat. No. G-1160; Sigma), 1:1000 dilution; anti-lck polyclonal antibody (2102, Cat. No. sc-13; Santa Cruz Biotechnology, Inc., Santa Cruz, Calif., U.S.A.), 5 $\mu$g/ml; p-nitrophenyl phosphonate transition state analogue conjugated to bovine serum albumen (NBP-BSA; Tawfik et al, 1993; Tawfik et al., 1997), 5 $\mu$g/ml. PBS was used as buffer for the incubation and wash steps as described (Nissim et al., 1994).

All the constructs tested were positive in ELISA using suitable affinity reagents.

Figure 3:
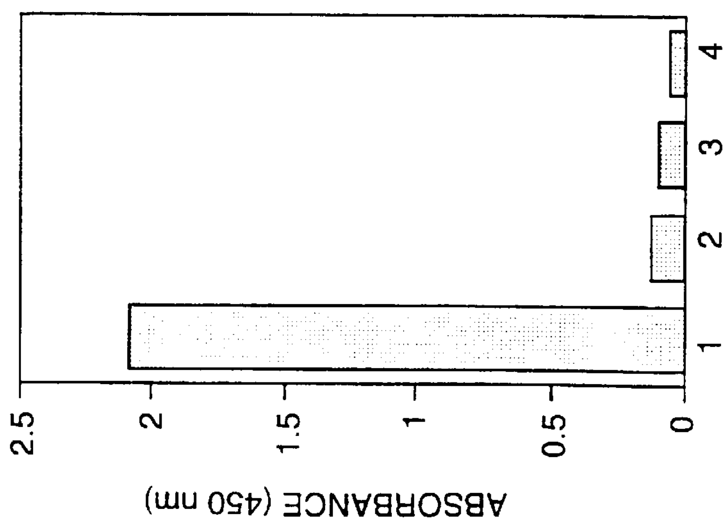
FIG. 3 shows the ELISA detection of calmodulin tagged construct pDN323 binding to biotinylated peptide in the presence (1) or, absence (4) of calcium; a non-specific phage (2) and milk instead of phage (3) were also tested.

FIG. 3 shows the ELISA results relative to construct pDN323, which displays calmodulin as a gene III fusion. Calmodulin-tagged phage DN323 showed binding to a biotinylated derivative of peptide CAAARWKKAFIAVSAANRFKKIS (Montigiani et al., 1996) in the presence (1), but not in the absence (4) of calcium. A non-specific phage (2;

GST-phage fusion FV7) and use of milk instead of phage (3) were also negative. Similar results were reproducibly obtained with other calmodulin-tagged phages. Phage particles not displaying calmodulin did not react in this assay.

Figure 4:
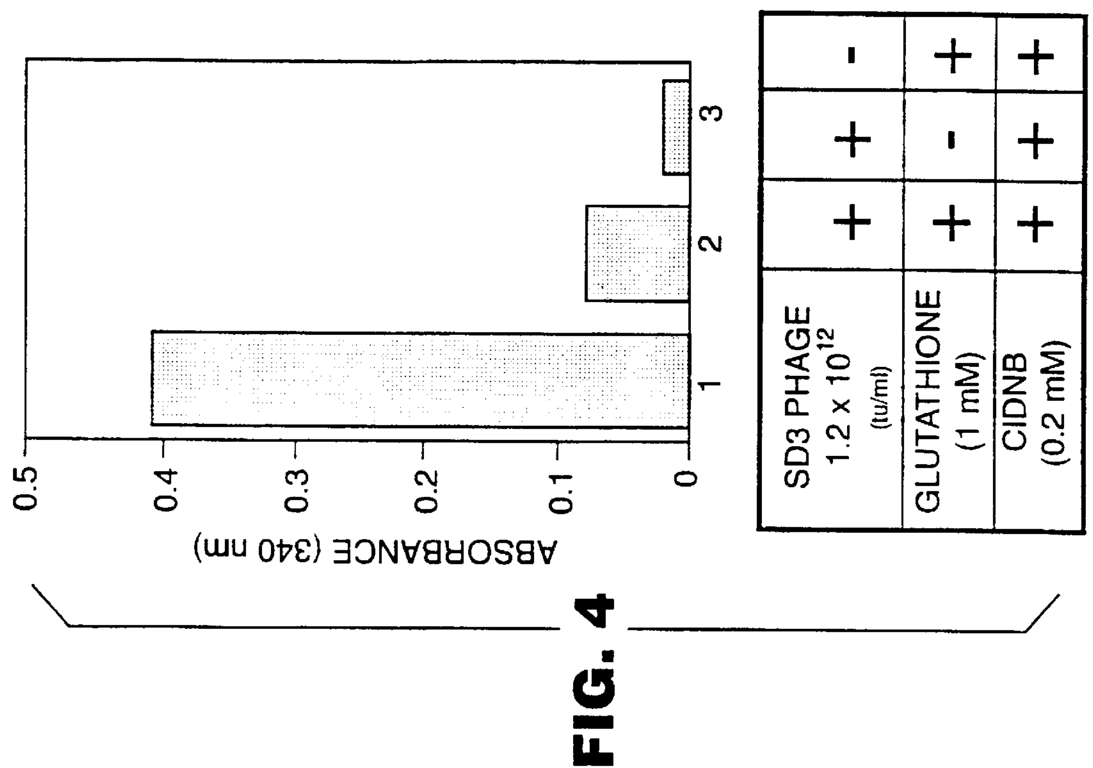
FIG. 4 shows stability of the complex between calmodulin fusions on filamentous phage and peptide derivatives.

The presence of enzymatic activity was confirmed for phage displaying a glutathione S-transferase-calmodulin fusion (construct pSD3; FIG. 2), using a standard colorimetric assay with glutathione and 1-chloro-2,4-dinitrobenzene as reaction substrates (Habig et al., 1974). The results are shown in FIG. 4. Negligible conversion to product occurred in the absence of either glutathione or ϕSD3 phage.

Example 4

Stability of the Complex Between Calmodulin Fusions on Filamentous Phage and Peptide Derivatives.

The selection methodology relies on a stable complex forming between the calmodulin-binding peptide derivative and calmodulin. The stability of this interaction was tested in two ways.

In parallel reactions, phages displaying calmodulin were incubated with biotin-labeled high-affinity (biotin-CAAARWKKAFIAVSAANRFKKIS) and medium-affinity (biotin-CAAARAKKNFIAVSAANRFKKIS) (SEQ ID NO: 16) calmodulin binding peptides (Montigiani et al., 1996).

A $10^{-8}$ M solution of a biotinylated calmodulin-binding peptide (CAAARWKKAFIAVSAANRFKKIS or CAAARAKKNFIAVSAANRFKKIS; Montigiani et al., 1996) was added to calmodulin-tagged phage preparations ($10^{12}$ transforming units/ml) in TBSC and incubated for 10 minutes. To the resulting mixture, aliquoted in different tubes, unlabeled CAAARWKKAFIAVSAANRFKKIS peptide in 1000-fold molar excess ($10^5$ M) was added at different times. The fraction of phage particles in which the biotinylated peptide had been replaced by the unlabeled peptide was then determined by ELISA as described above.

Stability of (calmodulin-tagged phage)/peptide complexes to PEG precipitation was checked as follows. A $10^{-8}$M solution (final concentration) of a biotinylated calmodulin-binding peptide CAAARWKKAFIAVSAANRFKKIS was added to 1 ml of calmodulin-tagged phage ($10^{12}$ transforming unit/ml) in TBSC and incubated for 10 minutes. To this solution, 20% polyethyleneglycol ($M_w$6000)+2.5M NaCl was added (200 $\mu$l) and the resulting mixture was incubated on ice for 1 hour, then centrifuged on a bench centrifuge (13,000 rpm; 5 minutes).

The pellet was resuspended in 1 ml of TBSC. The titre of the phage solutions before and after PEG precipitation were then determined. The fraction of phage particles that were still peptide-bound after the PEG precipitation procedure was evaluated by ELISA, using a streptavidin-coated plate (see above).

Figure 5:
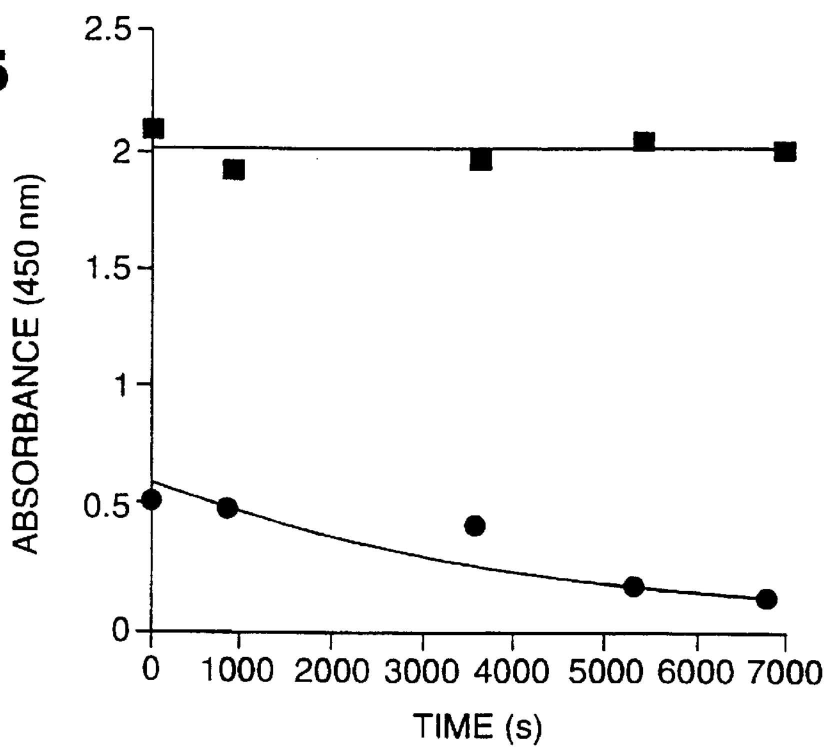
FIG. 5 illustrates the results of a competition assay of (calmodulin-tagged phage DN323)/(biotin-peptide) complex with a 1000-fold molar excess of unlabeled calmodulin binding peptide detected by ELISA.

The results of a competition assay of (calmodulin-tagged phage DN323)/(biotin-peptide) complex with a 1000-fold molar excess of non-biotinylated calmodulin-binding peptide, detected by ELISA are illustrated in FIG. 5. Squares: CAAARWKKAFIAVSAANRFKKIS; circles, CAAARAKKNFIAVSAANRFKKIS. These results show that only the high-affinity binding peptide forms a complex stable for more than 2 hours ($k_{off}$<$10^{-4}s^{-1}$).

FIG. 6 shows the results of an ELISA assay, illustrating the stability of a calmodulin-tagged phage DN323/biotin-CAAARWKKAFIAVSAANRFKKIS complex upon PEG precipitation, as detected by ELISA on streptavidin-coated plate. The difference in ELISA binding activity between the sample before (1) and after (2) PEG precipitation corresponds to a small loss in phage titre, as determined by *E.coli* infection and titration. In sample 3, 2% milk in TBSC was used instead of phage.

Therefore, the calmodulin/(biotin-CAAARWKKAFIAVSAANRFKKIS) complex is stable even after PEG precipitation. This is important whenever reactants have to be removed from the phage solution before the capture step.

Example 5

Selection and Amplification of Calmodulin-tagged Phage Particles.

We investigated whether calmodulin-tagged phage could be rescued and amplified by biopanning using the calmodulin-binding peptide derivative biotin-CAAARWKKAFIAVSAANRFKKIS.

This model compound mimicks the product of a bimolecular covalent bond-forming reaction, in which one of the two reagents is coupled to the peptide and the other reagent is biotinylated.

Biopanning experiments were performed as described in Example 4. As summarised in Table 1, phage displaying the glutathione S-transferase-calmodulin fusion were mixed with a 1000-fold molar excess of phage displaying only glutathione S-transferase (GST), and incubated with biotin-CAAARWKKAFIAVSAANRFKKIS. The resulting mixture was then selected using streptavidin-coated magnetic beads and amplified by bacterial infection.

A similar selection experiment was performed with phages displaying a tyrosine kinase (Table 1). PCR screening of infected bacterial colonies revealed an enrichment factor of at least 20,000:1 in a single round of panning. Selection of calmodulin-tagged phage at greater dilutions (1:$10^6$; Table 1) led to an enrichment factor greater than $10^6$:1 after two rounds of panning. This excellent selectivity is the result of the high-affinity capture reagent (streptavidin) and of the mild and selective elution protocol used (calcium chelation by EDTA).

In Table 1, "input" phages are those used for the selection; "output" phages are those recovered after the biopanning procedure (but before *E.coli* amplification). *represents phages prepared from pSD3 and pFV7, respectively. E is enzyme; GST is glutathione S-transferase; IRK is the tyrosine kinase domain of the insulin receptor; CaM is calmodulin. #: the sum of A+B is equal to the total amount of colonies screened by PCR.

TABLE 1

| INPUT | | | Round of | OUTPUT | | |
|---|---|---|---|---|---|---|
| Titre A E-CaM-fd* (t.u./ml) | Titre B E-fd* (t.u./ml) | Ratio A/B | Selection (enzyme E) | Titre (t.u./ml) | Ratio # A/B | Enrichment |
| 5 × $10^7$ | 5 × $10^{10}$ | 1:$10^3$ | 1 (GST) | 7 × $10^5$ | 40:0 | >4 × $10^4$ |
| 3 × $10^8$ | 3 × $10^{11}$ | 1:$10^3$ | 1 (IRK) | 5 × $10^5$ | 26:1 | 2.6 × $10^4$ |
| 1 × $10^6$ | 1 × $10^{12}$ | 1:$10^6$ | 2 (GST) | 5 × $10^7$ | 20:0 | >2 × $10^7$ |
| 5 × $10^4$ | 5 × $10^{10}$ | 1:$10^6$ | 2 (GST) | 2 × $10^7$ | 20:0 | >2 × $10^7$ |
| 6 × $10^3$ | 6 × $10^9$ | 1:$10^6$ | 2 (IRK) | 1 × $10^5$ | 15:4 | 3.8 × $10^6$ |
| 6 × $10^5$ | 6 × $10^{11}$ | 1:$10^6$ | 2 (IRK) | 5 × $10^5$ | 11:8 | 1.4 × $10^6$ |

Example 6

Isolation of Phage Expressing Active Enzyme over Inactive Phage Through Selection of Reaction Product.

1) Lck Tyrosine Kinase Phosphorylates a Peptide Substrate

The efficiency of our enzyme selection scheme was tested using the catalytic domain of the lck tyrosine kinase as enzyme, a synthetic peptide as substrate and GST-SH2 fusion (glutathione transferase-Src homology 2 region) as affinity reagent.

The Y505→F mutant of lck from murine cDNA was used as active enzyme.

The K273→A mutant of lck from murine cDNA was used as inactive enzyme.

The two catalytic domains were PCR-amplified (94° C.{1'}–60° C.{1'}–72° C.{2'}, 25 cycles) using oligonucleotides LCKfonot (5' ATG CAA TGA TGC GGC CGC AGG CTG AGG CTG GTA CTG GCC CTC 3') and LCKbanco (5' TCT ATA GCC ATG GCC CAG GTG CAG AAG CCC CAG AAG CCG TGG TGG 3'), which append a Nco1 site and a Not1 site at the extremities of the PCR fragment.

The fragment was then NcoI/NotI digested and subcloned into the NcoI/NotI sites of phagemid pDN327 (Example 1). The corresponding phage particles displaying tyrosine kinase-calmodulin-pIII fusion on filamentous phage were produced according to standard methodology (Nissim et al., 1994). Phage particles were positive in phage ELISA, immobilising on the plate either biotinylated CAAARWKKAFIAVSAANRFKKIS or a commercially available rabbit polyclonal anti-lck antibody (Santa Cruz Biochemicals), using protocols similar to those described in Example 1. Enzyme activity of such phage particles was tested using γ-$^{32}$ATP as phosphate donor and tyrosine containing specific peptide LUCK-1 and enolase as substrates.

The peptides LUCK+ (EPQYEEIGAARWKKAFIAVSAANRFKKIS) (SEQ ID NO: 17) and LUCK- (EPQFEEIGAARWKKAFIAVSAANRFKKIS)(SEQ ID NO: 18) are synthetic calmodulin binding ligands that have a short peptide appended at the carboxy terminus. LUCK+ is a substrate for lck, through the presence of a tyrosine residue at position 4 in the sequence (underlined). LUCK– has a phenylalanine residue at this position and is thus not a substrate of the lck tyrosine kinase.

Peptides were synthesized on a solid phase using a model 350 multiple peptide synthesizer (Zinsser Analytic, Frankfurt, Germany) employing Fmoc/t-butyl protecting groups. The Fmoc group was cleaved by 20% (v/v) piperidine in dimethylformamide and successive amino acids were added as N-hydroxybenzotriazole esters. The peptides were deprotected and cleaved from the resin by 93% trifluroacetic acid; 3% 1,2-ethanediol; 2% thioanisole; 2% water. Peptides were analyzed by HPLC using a Vydac C18 column (10 μM, 100×250 mm) and by amino analysis (PICO TAG, Waters, Milford, Mass.).

As affinity capture reagent a GST-fusion of the N-terminal SH2 domain of PI 3-kinase was used, subcloned in pGEX vector (Pharmacia) and affinity-purified on glutathione agarose. The GST-SH2 fusion was coated on Nunc Immunotubes (4 ml; 100 μg/ml in PBS) at room temperature overnight. The tubes were then washed and incubated for 2 hours with 3% BSA in phosphorylation buffer (30 mM HEPES, pH 7.4, 150 mM NaCl, 12 mM $MgCl_2$, 1 mM sodium vanadate, 1 mM $CaCl_2$).

The selection procedure was tested by incubating $10^{12}$ transforming units of active phage (Y505→F), inactive phage (K273→A) and phage from pSM5 (Example 1) with 0.5 nM LUCK+ in phosphorylation buffer for 1 hour. ATP was then added to a final concentration of 100 μM. After one minute, the mixtures were loaded onto separate GST-SH2-coated immunotubes and incubated for 30 minutes. The tubes were then washed 10 times with TBS+1 mM $CaCl_2$ (TBSC)+0.1% Tween-20 and 10 times with TBSC. The phage bound to the tube via the phosphorylated peptide was specifically eluted with 1 ml 10 mM EGTA in PBS (Neri et al., 1995) that causes dissociation of the peptide ligand from calmodulin present in the fusion protein presented on the phage.

The eluted phage was used to infect exponentially growing TG1 *E. coli* cells according to standard procedures (Nissim et al., 1994), then plated on selective ampicillin-glucose-TY plates. Ampicillin-resistant transformants were counted and used to calculate the titre of the phage recovered in the selection procedure. The titre of phage recovered from the active phage selection was >50 times higher than the titre of phage from the inactive phage and scFv(D1.3)-CaM-phage selections. The same procedure performed with LUCK-peptide resulted in low phage titres recovered in all three cases.

2) The Insulin Receptor Tyrosine Kinase Phosphorylates a Peptide Substrate.

The efficiency of the enzyme selection scheme was further proven using the catalytic domain of the insulin receptor tyrosine kinase as enzyme, a synthetic peptide as substrate and antiphosphotyrosine antibody as affinity reagent.

The phage clone ϕAH1 (expressing pAH1) that display the pIII/calmodulin/kinase catalytic domain was selected against another clone ϕSD3 (expressing pSD3) that display the pIII/calmodulin/glutathione-S-transferase fusion. The reaction product (phosphotyrosine) was captured with a biotinylated α-phosphotyrosine antibody (RC20; Transduction Laboratories, Lexington, Ky.). As a negative control, the experiment was repeated with ϕAH1 but without the peptide substrate.

A peptide was synthesized that is a substrate of the insulin receptor tyrosine kinase and that contains a calmodulin binding sequence. As described by Shoelson et al. (1992) the sequence YMNM (underlined) is a very good substrate for this tyrosine kinase. The C-terminal part of the peptide possesses calmodulin binding activity (in bold). Montigiani et al. (1996) have shown that the sequence CAARWKKAFIAVSAANRFKKIS binds to calmodulin with a $K_D$ of $2.2\times10^{-12}$M.

In order to bridge the distance between the catalytic site of the kinase and the calmodulin, we have introduced as a spacer, additional amino acids between the calmodulin binding region and the substrate sequence.

TGDYMNMSPVGAAARWKKAFIAVSAANRFKKIS (SEQ ID NO: 19)

The peptides were made according to the protocol set out above in Example 6 on a solid phase using a model 350 multiple peptide synthesiser.

In order to demonstrate that the peptide binds to calmodulin, we have performed a bandshift assay (Neri et al., 1995). A 20 μl reaction was set up containing 15 μg peptide and 12 μg calmodulin in TBSC (50 mM Tris.HCl pH7.4; 100 mM NaCl; 1 mM $CaCl_2$). 5 μl of gel loading mix (4 g sucrose, 25 mg bromophenol blue in 10 ml) were added, and 13 μl of each reaction resolved on a native 16% polyacrylamide gel at 140V. Neither the gel nor the electrophoresis buffer contained SDS (sodium dodecyl sulphate). The gel was stained with Coomassie blue.

The reactions were performed in different tubes at 30° C. in the labelling buffer (50 mM Hepes pH7.4; 100 mM NaCl;

10 mM $MnCl_2$; 0.5 mM $NaVO_3$; 0.5 mM $CaCl_2$; 10 $\mu$g/ml Pefabloc (Boehringer Mannheim); 200 $\mu$M ATP). The phage solution (containing the amount of transforming units shown in Table 2) was preincubated for 20 minutes. The peptide was added to a final concentration of 5 nM and incubated for 15 minutes. The phages were precipitated by addition of ⅕ volume of 2.5M NaCl and 20% $PEG_{6000}$, put on ice for 15 min and centrifuged for 3 min at 13,000 rpm.

The phage pellet was resuspended in 0.5 ml TBSC, the biotinylated α-phosphotyrosine antibody ($10^{-8}$ M) was added to this suspension and incubated for 10 minutes. The phage/peptide/antibody complex was transferred to $4.7\times10^7$ streptavidin coated Dynabeads (M-280; Dynal, Oslo, Norway) that had been preblocked with 2% BSA in TBSC. The beads were carefully washed on a magnet, 5 times with TBSC containing 0.1% Tween-20 and 5 times with TBSC alone. The phages were eluted by addition of 20 mM EDTA in TBS (5 min) and were then transferred to a fresh tube. In order to neutralise the EDTA, 40 mM $CaCl_2$ was added.

The resulting suspension was used to infect exponentially growing TG1-bacteria for 30 min at 37° C., without shaking. The infected bacteria were plated and counted on agar plates containing ampicillin. The results are shown in Table 2.

The amount of phage we used for the selection assay is indicated in the input column. After selection the amount of phages was determined by infection of colony building bacteria (output).

TABLE 2

| Phage φ | Input (tu/ml)* | Output (tu/ml) | Enrichment ratio+ |
|---|---|---|---|
| (a) | | | |
| φAH1 | $6 \times 10^{10}$ | $1 \times 10^5$ | |
| φSD3 | $1 \times 10^{11}$ | $1 \times 10^3$ | 167x |
| (b) | | | |
| φAH1 (with peptide) | $1.5 \times 10^{11}$ | $1.5 \times 10^4$ | |
| φAH1 (without peptide) | $1.5 \times 10^{11}$ | $2 \times 10^3$ | 7.5x |

*transforming units/ml
+enrichment of φAH1 over φSD3 = [Out (φAH1/φSD3) ] / [In (φAH1/φSD3) ].

The results of the bandshift assay indicate that the peptide binds to calmodulin. The selection experiment demonstrates that a phage displaying a functional kinase can be amplified 167× over a phage enzyme fusion catalysing a different reaction (Table 2(a)). In Table 2(b) it can be seen that the phage enzyme incubated with the peptide is captured more efficiently than the phage enzyme missing its specific substrate.

3) Selection of Active Glutathione S-transferase Enzyme Displayed on Phage.

A similar procedure to that described above is applicable to phage expressing glutathione S-transferase. A derivative of a glutathione S-transferase (GST) substrate has been prepared that is capable of calmodulin binding.

1-Chloro-2,4-dinitrobenzene is an excellent substrate of GST, which readily reacts with glutathione in a catalysed reaction. We have shown that 4-Chloro-3-nitrobenzaldehyde derivatives in which the aldehyde moiety has reacted with a primary amine to form a Schiff base is an excellent substrate for the same reaction.

We therefore synthesized a derivative of the calmodulin binding peptide CAAARWKKAFIAVSAANRFKKIS initially described by Montigiani et al. (1996), modified with 4-chloro-3-nitrobenzadehyde (Aldrich, Buchs, CG) in a way that preserved the calmodulin-binding activity of the peptide.

A derivative of the calmodulin binding peptide CAAARWKKAFIAVSAANRFKKIS was used that contains at the N-terminus two extra amino acid residues to act as spacers (CGGAAARWKKAFIAVSAANRFKKIS)(SEQ ID NO: 20). The thiol group of the N-terminal cysteine residue was used for the site-specific conjugation to a 4-chloro-3-nitrobenzaldehyde derivative, obtained by conjugation of this aldehyde with 4(4-N-maleimidomethyl) cyclohexane 1-carboxyl hydrazide (Pierce, Rockford, Ill.).

The synthesis was performed as described above. 4-Chloro-3-nitrobenzaldehyde (0.24 mg, $1.3\times10^{-3}$ mmol) and 4(4-N-maleinidomethyl) cyclohexane 1-carboxyl hydrazide (0.19 mg, $6.6\times10^{-4}$ mmol) were dissolved in 200 ml of DMSO and left at room temperature.

After 30 min, TRIS buffer (0.16 mg, $1.3\times10^{-3}$ mmol) dissolved in 100 ml of water was added to block the unreacted aldehyde by formation of a Schiff base (20 min).

As a last step, peptide CGGAAARWKKAFIAVSAANRFKKIS (0.50 mg, $1.9\times10^{-4}$ mmol) dissolved in 200 ml of water was added to the adduct 4-Chloro-3-nitrobenzaldehyde-4(4-N-maleimidomethyl) cyclohexane 1-carboxyl hydrazide; this reaction proceeded at room temperature for 30 minutes and the reaction product was purified by cation exchange chromatography as described by Neri et al., 1995 and Montigiani et al., 1996.

This peptide ($10^{-8}$M) was incubated with phage in the presence of glutathione (GSH; $10^{-5}$M) biotinylated at the N-terminal position. A mixed phage population was used, comprising phage displaying GST-CaM as gene III-product fusion (from vector pSD3) and an equimolar amount of phage displaying insulin receptor tyrosine kinase-CaM as gene III-product fusion (from vector pAH1) in 1 ml TBSC containing 2% BSA. The ratio of input phage was confirmed by infection of *E. coli* and subsequent PCR screening of single isolated colonies, using oligos LMB3 and fdseq 1 (5'-GAATTTTCTGTATGAGG-3'(SEQ ID NO: 21)).

After 5 minutes incubation, 20% polyethyleneglycol 6000+NaCl was added (200 $\mu$l ) and the resulting mixture incubated on ice for 1 hour, before centrifugation on a bench centrifuge (13,000 rpm; 5 minutes). The pellet was resuspended in 1 ml TBSC, then 100 $\mu$l streptavidin-coated M280 Dynabeads (Cat. no. 112.05; 10 mg beads/ml; DYNAL, Oslo, Norway), preblocked in TBSC containing 2% BSA, were added. The tubes were mixed for 10 minutes and the magnetic beads were captured on a magnet (Cat. no. 120.04; DYNAL) and washed 5 times with TBSC+0.1% Tween-20, then 5 times with TBSC.

Phages were eluted with TBSE (5 minutes incubation) saturated with calcium, used to infect exponentially growing TG1 *E. coli* cells (Gibson, 1984), then plated on TYE agar plates containing 100 mg/ml ampicillin and 1% glucose. The ratio of the two phages after selection was obtained by PCR screening of single colonies (Marks et al., 1991), using oligos LMB3 and fdseq1 (5'-GAATTTTCTGTATGAGG-3').

The results are shown below in Table 3. The ratio of output GST-CaM-fd phage compared to IRK-CaM-fd phage was shown to be 18:2. This corresponds to a 15-fold enrichment of active GST enzyme over the control enzyme inactive in the selection reaction.

TABLE 3

| INPUT | | | | OUTPUT | |
|---|---|---|---|---|---|
| Titre A GST-CaM-fd (t.u./ml) | Titre B IRK-CaM-fd (t.u./ml) | Ratio A/B | Rounds of Selection | Titre (t.u./ml) | Ratio A/B |
| $4.2 \times 10^{10}$ | $6.5 \times 10^{10}$ | 1:1.5 | 1 | $3 \times 10^{6}$ | 18:2 |

Example 7

Alternative Tagging Methodologies

1) Development of Phage Expressing Mutant ScFvs.

To exemplify a tagging methodology that utilises selective and site-specific chemical labeling, rather than binding pairs, we displayed on filamentous phage an ScFv derivative of antibody D2.3. This antibody was elicited by immunisation with the transition state analogue NBP, and which catalyses the hydrolysis of p-nitrobenzyl ester (NBE).

Cysteine mutants of this scFv fragment were then generated, at the following six positions in the heavy and light chains of the molecule; Threonine H30, Threonine H31, Serine H57, Serine L27, Serine L56 and Serine L52. Analysis of the structure of a large number of antibodies elicited using small synthetic antigens has indicated that these residues are part of the hypervariable regions yet in most antibodies they do not interact directly with the hapten. Moreover, the selected residues are solvent exposed in most murine antibodies and their modification should have minor effects on the overall structure and activity of the antibody. These positions are also highly conserved in most murine antibodies and hence in phage-antibody libraries based on murine sequences. Analogous positions can be identified in other antibodies (e.g., human antibodies) and in enzymes.

The cysteine mutants were constructed using overlapping PCR. Two fragments were amplified by PCR with plasmid D2.3-pCANTAB (Se-Ho Kim, Ph.D thesis, Weizmann Institute of Science, 1997) as template using primers carrying each mutation. The primers used were as follows: Thr30-Back: (CAAGAC-TTCTGGATACATCTTCTGCAGCTACTG-GATTCACTGGGTAAAAC (SEQ ID NO: 22)(the codon encoding for Cys30 is underlined) and fdSEQ1: (GAATTTTCTGTATG-AGG) for amplifying one fragment and Thr30-Forward: (GCAGAAGATGTATCCAGA-AGTGTTG) (SEQ ID NO: 23) and pCANTAB-SEQ1: (TTGGAGATTTTCAACGTG) (SEQ ID NO:23) for amplifying the second fragment.

These fragments were then assembled by a subsequent PCR using primers fdSEQ1 and pCANTAB-SEQ1 and plasmid D2.3-pCANTAB as template. The PCR products were purified by agarose gel electrophoresis, digested with restriction enzymes NcoI and NotI and ligated into plasmid pHEN1 (Harrison et al., 1996; Hoogenboom et al., 1991) digested with the same enzymes. The resulting plasmids (D2.3-pHEN-) were transformed into *E. coli*-TG1 bacteria and phagemid particles were produced as described by Harrison et al., 1996. In general, phage titres of all six cysteine mutants were low relative to the wild type, yet infectivity was retained.

Conditions were optimised so that relatively high titres of phages displaying active antibodies could be obtained. In particular, growing the bacteria carrying the plasmids encoding for the cysteine mutants (after infection with VCS-M13 helper phage) at 25° C. gave high titres. The growth of bacteria at various temperatures is shown in FIG. 7.

The phage particles displaying the cysteine mutants of antibody D2.3 were purified by PEG-precipitation and analysed by phage-ELISA on NBP-BSA as described above. All the cysteine mutants except L27 exhibited binding activity. Phage mutants L56 and H57 exhibited binding activity that is only slightly lower than that observed in the parental D2.3 phage antibody. The results of the phage ELISA are shown in FIG. 8. Results are given in optical density at 450 and 650 nm at 1:25 phage dilution.

The phages carrying the cysteine mutants of D2.3-ScFv were used to re-infect *E.Coli*-TG1 bacteria that do not carry the D2.3-pHEN plasmid and to produce new particles that carry D2.3-ScFv (as demonstrated by phage ELISA). Hence, the cysteine mutation did not affect the infectivity of the phage particles.

These results demonstrate that certain conserved residues or positions that are close to the active site and solvent exposed can be mutated to cysteine with the resulting ScFv retaining binding activity. The positions modified are conserved in murine antibodies and are hence suitable for modification not only in a single antibody but also in a library that encodes for a larger repertoire. Moreover, phage particles that display these cysteine mutants (fused to coat protein pIII) are infective and hence a basic requirement for selection is met.

2) Specific, Covalent Linking of Ligands to Phage Particles Displaying the Cysteine Mutants of D2.3-ScFv.

This approach to tagging is based on the intramolecular reaction of the enzyme to be selected with a covalently linked substrate. For this approach to work successfully, reagents and conditions must be used under which a negligible amount of substrate links to wild type phage particles, or to phage particles displaying an antibody that does not carry the cysteine mutation.

To demonstrate the above, the following samples of phages were prepared: wild type phage VCS-M13, VCS-M13 phages displaying D2.3-ScFv antibody and VCS-M13 phages displaying the cysteine mutants either L56, L52 or H57 of D2.3-ScFv antibody. Biotin was used as a molecular probe. Linking of biotin, or a biotinylated ligand to phages could then be easily detected by avidin-phage ELISA as described above.

For the labelling experiments, the phages were further purified by resuspending the pellet after PEG precipitation in 2.5M urea and filtering through a Millipore 300 Kd units. Phages were rinsed several times with PBS, pH 7.0 containing 0.1% Tween-20 (PBS/T) and then with PBS. Phages were removed from the Millipore filters, DTT (10 $\mu$M) was added and the mixture incubated for 20 min at room temperature.

The phages were purified by PEG-precipitation and resuspended in 50 $\mu$l PBS ($10^8$–$10^9$ t.u.). The Biotin-HPDP reagent (Pierce) was dissolved in DMF, diluted 1:25 in 50 $\mu$l PBS and added to the DTT-treated, PEG-purified phages. The mixture was incubated for 20 min at 23° C. or 1 hr on ice. The modified phages were purified by PEG-precipitation (twice), diluted 10-fold in Marvel/PBS and the extent of biotin labelling determined by avidin-phage ELISA.

Phage ELISA was carried out broadly as described above; microtitre plates (Nunc; maxisorp) were coated with avidin (Sigma; 2 $\mu$g/well in 0.1 ml PBS buffer pH7.4; 14 hr at 4° C.) The plate was blocked with 2% Marvel/PBS and phages added. The number of phages labelled with biotin (and thus bound to the avidin-coated plate) was determined as in ordinary phage ELISA.

Results of this assay are given in Table 4 in optical density at 450 and 650 nm.

TABLE 4

Modification of phage particles with Biotin HPDP

| HPDP-Biotin Conditions | None 23° -20 min | 10 μM 23° -20 min | 10 μM 4° -1 hr | 100 μM 23° -20 min | 100 μM 4° -1 hr |
|---|---|---|---|---|---|
| | Optical Density (450/650 nm) | | | | |
| Phage | | | | | |
| VCS-M13 | 0.00 | 0.28 | 0.19 | 0.75 | 1.40 |
| M13-D2.3 | 0.00 | 0.26 | 0.22 | 0.63 | 1.40 |
| M13-D2.3-CysL56 | 0.00 | 0.91 | 0.30 | 1.41 | 1.39 |
| M13-D2.3-CysL52 | 0.00 | 1.05 | 1.08 | 1.26 | 1.49 |
| M13-D2.3-CysH57 | 0.00 | 0.75 | 0.59 | 1.67 | 0.85 |

These results clearly indicate that a ligand can be linked via the thiol of a cysteine residue introduced near the active site of a catalytic antibody and displayed on phage. Under the conditions described above, the non-specific labelling at other residues of the antibody or the phage particle is minimal. The possibility of a trans reaction (i.e., the formation of product linked to one phage particle catalysed by an active site presented by another phage) is therefore minimal.

3) Intramolecular Conversion of a Linked Substrate to Give a Product Bound to Specific Antibodies.

This selection approach is based upon the covalent linkage of the substrate at the vicinity of the active site of the enzyme via a flexible linker so that its conversion to the product can be catalysed intramolecularly. Phages expressing a catalytic variant can be selected by binding to antibodies that specifically bind this product and that do not cross-react with the substrate.

Structural modelling suggested that a 10–20Å linker should be long enough to link the antibody-bound substrate and the thiol group of a cysteine at positions L56, L52 or H57.

The p-nitrobenzyl ester substrate of antibody D2.3 was therefore linked via a 25 Å linker to a dithiopyridine group to allow its conjugation to phage particles carrying the cysteine mutants L56, L52 or H57 of ScFv-D2.3. This derivative (NBE-HPDP:

4—NO2—C6H4—CH2—O—C(=O)—(CH2)3—C(=O)—NH—(CH2)5—NH—C(=O)—NH—(CH2)2—S—S—(2-Pyridine) was synthesised from commercially available starting materials by modifying published procedures such as described by Tawfik et al., 1997. NBE-HPDP was reacted with phage particles carrying the cysteine mutants L52, L56 and H57 of antibody D2.3 using the procedure described above for the specific labelling with Biotin-HPDP (10 μM NBE-HPDP, 20 minutes incubation at 23° C.) The phages were purified by PEG precipitation (twice; on ice) to remove excess of NBE-HPDP and incubated in Tris buffer pH8.0 (50 μl; 30 min at 23° C.) to allow the ScFv-D2.3 displayed on them to catalyse the conversion of the covalently linked NBE substrate into the corresponding carboxylic acid product (HO—C(=O)—(CH2)3—C(=O)—NH—(CH2)5—NH—C(=O)—NH—(CH2)2—S— linked to ScFv-D2.3 displayed on the phage).

Binding of the phage particles to antibodies directed against the carboxylic acid product of the NBE substrate was then determined by phage ELISA as follows; microtitre plates were coated with goat anti-rabbit antibodies (Sigma, 2.5 μg/well in 0.1 ml phosphate buffer pH7.4; 2 hr at room temperature) and then treated with rabbit serum, that binds the carboxylic acid product of the NBE substrate with high specificity and affinity (Tawfik et al., 1993). Bound phage particles were detected with antibodies against M13 phage labelled with peroxidase as described by Harrison et al., 1996.

The results of this assay indicate that the cysteine mutants odified with NBE-HPDP bind to the anti-product antibodies coated on the plate. In control experiments, phage particles displaying the cysteine mutants and modified with NBE-HPDP in the presence of 100 μM of the soluble NBP hapten (which is a potent inhibitor of D2.3; Tawfik et al., 1997) showed significantly lower binding. The inhibition of the ELISA signal by the NBP hapten indicates that the conversion of the covalently-linked NBE substrate into the corresponding product was indeed catalysed by the phage-displayed ScFv-D2.3. Moreover, the background signal observed in the presence of phage particles displaying just D2.3, or phage particles displaying the cysteine mutants that were not modified with NBE-HPDP, was significantly lower.

This demonstrates that the substrate can be covalently linked at the vicinity of the active site of a catalytic antibody via a flexible linker and intramolecularly converted to product. This results in the specific binding of those phage particles displaying the catalytic antibody to antibodies that bind that product.

REFERENCES

Bass, S., Greene, R. and Well, J. A. (1990) *Protein Struct. Funct. Genet.* 8, 309–314

Chester, K. A., Begent, R. H., Robson, L., Keep, P., Pedley, R. B., Boden, J. A., Boxer, G., Green, A., Winter, G., Cochet, O. and Hawkins R. E. (1994) *Lancet,* 343, 455–456.

Corey, D. R., Shiau, A. K., Yang, Q., Janowski, B. A. and Craik, C. S. (1993) Gene 128, 129–134.

Cunningham, B. C., and Wells, J. A. (1987) *Protein Eng.,* 1, 319–325.

Figini, M., Marks, J. D., Winter, G. and Griffiths A. D. (1994) *J. Mol. Biol.* 239, 68–78.

Gibson, T. J. (1984) Studies on the Epstein-Barr virus genome. Ph.D. Thesis, University of Cambridge.

Habig, W. H., Pabst, M. J. and Jakoby, W. B. (1974). *J. Biol. Chem.,* 249, 7130–7139.

Harrison, J. L., Williams, S. C., Winter, G. & Nissim, A. (1996) *Methods in Enzymology* 267, 83–109.

Hoogenboom, H. R., Griffiths, A. D., Johnson, K. S., Chiswell,

D. J., Hudson, P. and Winter, G. (1991) *Nucl. Acids Res.,* 19, 4133–4137.

Hermanson, G. T. (1996) *Bioconjugate techniques.* Academic Press, San Diego.

Hopp, T. P., Prickett, K. S., Price, V. L., Libby, R. T., March, C. J., Cerretti, D. P., Urdal, D. L. and Conlon, P. J. (1988). *Bio/Technology* 6, 1204–1210.

Hubbard, S. R., Wei, L., Ellis, L. and Hendrickson, W. A. (1994). *Nature,* 372, 746–754.

Illangasakere, M., Sanchet, G., Nickles, T. and Yanus, M. (1995). *Science,* 267, 643–647.

Jespers, L., Messens, J. H., De Keyser, A., Eeckhout, D., Van Den Brande, I., Gansemans, Y. G., Lauwereys, M. J., Vlasuk, G. P. and Sanssens, P. E. (1995) *Bio/Technology* 13, 378–382.

Kang, A. S., Jones, T. M. and Burton, D. R. (1991) *P.N.A.S. USA,* 88, 4363–4366.

Kim, S-H., PhD Theis, Weizmann Institute of Science, 1997.

Lonsch, J. R. and Stostak, J. W. C. (1994) *Science,* 371, 31–36.

Marks, J. D., Hoogenboom, H. R., Bonnert, T. P., McCafferty, J., Griffiths, A. D. and Winter, G. (1991) *J. Mol. Biol.,* 222, 581–597.

McCafferty, J., Griffiths, A. D., Winter, G. and Chiswell, D. J. (1990) *Nature* 348, 552–554.

McCafferty, J., Jackson, R. H. and Chiswell, D. J. (1991). Protein Engineering, 4, 955–961.

Montigiani, S., Neri, G., Neri, P. and Neri, D. (1996) *J. Mol. Biol.,* 258, 6–13.

Neri, D., de Lalla, C., Petrul, H., Neri, P. and Winter, G. (1995). Bio/Technology [13], 373–377.

Neri, D., Petrul, H., Light, Y., Marais, R., Britton, K. E., Winter, G. and Creighton, A. M. (1996). *Nature Biotechnology,* 14, 385–390.

Nissim, A., Hoogenboom, H. R., Tomlinson, I. I., Flynn, G., Midgley, C., Lane, D. and Winter, G. (1994) *EMBO J.,* 13, 692–698.

O'Neil, K. and DeGrado, W. (1989) *Proteins* 6, 284–293.

Sambrook et al., Molecular cloning, a laboratory manual (1989) Cold Spring Harbor Press.

Smith, G. P. (1985). *Science,* 228, 1315–1317.

Soumillion, P., Jespers, L., Bouchet, M., Marchand-Brynaert, J., Winter, G. and Fastrez, J. (1994). *J. Mol. Biol.,* 237, 415–422.

Tawfik, D. S., Lindner, A. B., Chap, R., Eshhar, Z. & Green, B.S. (1997) *Eur. J. Biochem.* 244, 619–626.

Tawfik, D. S., Green, B. S., Chap, R., Sela, M. & Eshhar, Z. (1993) *Proc. Natl. Acad. Sci. USA* 90, 373–377.

Török, K. and Trentham (1994) *Biochemistry,* 33, 12807–12830.

Tramontano, A., Janda, K. D. and Lerner, R. A. (1986) *Science,* 234, 1566–1570.

Vaughan, T. J., Williams, A. J., Pritchard, K., Osbourn, J. K., Pope, A. R., Earnshaw, J. C., McCafferty, J., Hodits, R. A., Wilton, J. and Johnson, K. S. (1996). *Nature Biotechnol.,* 14, 309–314.

Wilkinson, A. J., Fersht, A. R., Blow, D. M., Carter, P. and Winter, G. (1984) *Nature,* 307, 187–189.

Winter, G., Fersht, A. R., Zoller, M. and Smith, M. (1982) *Nature,* 299, 756–758.

EP-B-0161937, Nagai, K. and Thorgerson, H. C.

EP-B-0035384, Rutter, W. J.

What is claimed is:

1. A method of isolating an enzyme having a desired chemical or biological activity the method comprising:

a) linking the enzyme to a substrate for the enzyme b) reacting the enzyme and substrate such that a product is produced which remains linked to the enzyme; and c) isolating the enzyme by selectively isolating the product linked to the enzyme.

2. A method according to claim 1 in which the enzyme and substrate are linked via a binding pair.

3. A method according to claim 2 in which the binding pair are a calcium dependent binding polypeptide and a ligand thereof.

4. A method according to claim 3 in which the calcium dependent binding polypeptide is calmodulin or a derivative of calmodulin that retains binding activity, and the ligand of the calcium dependent polypeptide is a calmodulin ligand or derivative of a calmodulin ligand that retains calmodulin binding activity.

5. A method according to claim 2 in which the binding pair bind with a dissociation constant ($K_d$) of 10 nM or less, measured at a pH of between 6 and 9 at 20° C.

6. A method according to claim 5 wherein the dissociation constant is 1 nM or less.

7. A method according to claim 1 in which the enzyme and substrate are linked covalently.

8. A method according to claim 1 wherein the enzyme is displayed on a support containing a DNA encoding the enzyme.

9. A method according to claim 8, wherein the support is a bacteriophage particle.

10. A method according to claim 1 wherein the enzyme is isolated by binding the product to a solid matrix.

11. A method according to claim 10, wherein the solid matrix is suitable for biopanning.

12. A method according to claim 10 wherein the solid matrix is suitable for affinity chromatography.

13. A method according to claim 10, wherein the product is bound to the solid matrix by an antibody bound to the solid matrix.

14. A method according to claim 10 comprising a further step of dissociating the enzyme from the product bound to the solid matrix.

15. A method according to claim 10 wherein the dissociation of enzyme from the product is achieved by the use of a calcium chelator.

16. A method according to claim 1 wherein the enzyme is produced in an expression library.

17. A method according to claim 1 wherein the enzyme is produced by mutagenesis of a nucleic acid sequence.

* * * * *